United States Patent
Bachinski et al.

(10) Patent No.: US 11,872,404 B2
(45) Date of Patent: *Jan. 16, 2024

(54) SYSTEMS AND METHODS FOR WIRELESS CONTROL OF NONINVASIVE ELECTROTHERAPY

(71) Applicant: DJO, LLC, Vista, CA (US)

(72) Inventors: Thomas Jerome Bachinski, Lakeville, MN (US); Michael Wayne Moore, Oceanside, CA (US); Joseph Winn, Aliso Viejo, CA (US); Jay Dave, San Marcos, CA (US); David Orr, Vista, CA (US); Dain Silvola, Florence, OR (US)

(73) Assignee: DJO, LLC, Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/453,138

(22) Filed: Nov. 1, 2021

(65) Prior Publication Data
US 2022/0152404 A1 May 19, 2022

Related U.S. Application Data

(60) Division of application No. 16/126,822, filed on Sep. 10, 2018, now Pat. No. 11,160,986, which is a
(Continued)

(51) Int. Cl.
*A61N 1/372* (2006.01)
*A61N 1/04* (2006.01)
*A61N 1/36* (2006.01)

(52) U.S. Cl.
CPC ....... *A61N 1/37217* (2013.01); *A61N 1/0452* (2013.01); *A61N 1/0456* (2013.01);
(Continued)

(58) Field of Classification Search
CPC .. A61N 1/0492; A61N 1/0456; A61N 1/0452; A61N 1/36021
See application file for complete search history.

(56) References Cited

U.S. PATENT DOCUMENTS

| | | | | |
|---|---|---|---|---|
| 4,207,904 A | * | 6/1980 | Greene | A61N 1/0492 607/152 |
| 4,690,144 A | * | 9/1987 | Rise | A61N 1/37282 607/59 |

(Continued)

FOREIGN PATENT DOCUMENTS

| | | |
|---|---|---|
| CN | 101522254 A | 9/2009 |
| CN | 102421480 | 4/2012 |

(Continued)

OTHER PUBLICATIONS

Extended European Search Report dated Jul. 5, 2016 in patent application No. 14756730.9.
(Continued)

*Primary Examiner* — George R Evanisko
(74) *Attorney, Agent, or Firm* — KNOBBE, MARTENS, OLSON & BEAR LLP

(57) ABSTRACT

Methods and devices for providing noninvasive electrotherapy and electrical stimulation are described herein. In one aspect, a device for noninvasive electrotherapy includes wireless communication circuitry configured to receive pulse generation control signals wirelessly transmitted from a computing device. The device can include pulse generation circuitry configured to deliver electrical waveforms according to instructions encoded in the pulse generation control signals. The computing device can include a cellular telephone device, a portable media player, a personal digital assistant, a tablet computer, or an internet access device.

18 Claims, 19 Drawing Sheets

Related U.S. Application Data continuation of application No. 15/495,532, filed on Apr. 24, 2017, now Pat. No. 10,071,251, which is a division of application No. 14/191,146, filed on Feb. 26, 2014, now Pat. No. 9,630,013.

(60) Provisional application No. 61/771,636, filed on Mar. 1, 2013.

(52) U.S. Cl.
CPC ....... *A61N 1/0492* (2013.01); *A61N 1/36034* (2017.08); *A61N 1/37247* (2013.01); *A61N 1/36021* (2013.01)

(56) References Cited

U.S. PATENT DOCUMENTS

| | | | |
|---|---|---|---|
| 9,630,013 | B2 | 4/2017 | Bachinski et al. |
| 10,071,251 | B2 * | 9/2018 | Bachinski ............ A61N 1/0456 |
| 11,160,986 | B2 * | 11/2021 | Bachinski .......... A61N 1/37247 |
| 2006/0064139 | A1 | 3/2006 | Chung et al. |
| 2007/0123952 | A1 * | 5/2007 | Strother ............. A61N 1/36021 |
| | | | 607/48 |
| 2008/0027507 | A1 | 1/2008 | Bijelic et al. |
| 2009/0182393 | A1 | 7/2009 | Bachinski |
| 2009/0182394 | A1 * | 7/2009 | Bachinski ............ A61N 1/0452 |
| | | | 607/59 |
| 2010/0042180 | A1 | 2/2010 | Mueller et al. |
| 2010/0076533 | A1 | 3/2010 | Dar et al. |
| 2010/0286590 | A1 | 11/2010 | Durand |
| 2013/0023816 | A1 | 1/2013 | Bachinski et al. |
| 2013/0204169 | A1 * | 8/2013 | Poepperling ....... A61N 1/36021 |
| | | | 601/46 |
| 2013/0338729 | A1 | 12/2013 | Spector |
| 2014/0194946 | A1 * | 7/2014 | Thomas ............. A61N 1/36021 |
| | | | 607/46 |
| 2014/0324120 | A1 | 10/2014 | Bogie et al. |
| 2015/0165186 | A1 | 6/2015 | Dar et al. |
| 2022/0296908 | A1 | 9/2022 | Bachinski |

FOREIGN PATENT DOCUMENTS

| | | |
|---|---|---|
| WO | WO 08/028063 | 3/2008 |
| WO | WO 11/078966 | 7/2011 |

OTHER PUBLICATIONS

International Search Report for International Application No. PCT/US2014/018754 dated May 22, 2014.

* cited by examiner

| WAVEFORM SHAPES | | APPLICATIONS | GRAPHICAL REPRESENTATIONS |
|---|---|---|---|
| Monophasic Waveforms | Direct Current (DC) (Galvanic) | Iontophoresis, wound healing, denervated tissue | |
| | Interrupted DC (Pulsed Galvanic) | Edema reduction, wound healing, innervated muscle contraction | |
| Biphasic Waveforms | Symmetrical AC | Pain suppression, innervated muscle contraction | |
| | Asymmetrical AC | Pain suppression, innervated muscle contraction | |
| Triphasic Waveforms | Unbalanced Triphasic | Edema reduction, pain suppression | |

FIG. 6C

| START | STOP | PROGRAM |
|---|---|---|
| 03-11-12, 10:32 | 03-11-12, 10:37 | 1 |
| 03-12-12, 11:47 | 03-12-12, 11:48 | 1 |
| 03-17-12, 9:03 | 03-17-12, 9:08 | 1 |
| 03-19-12, 15:11 | 03-19-12, 15:19 | 2 |
| --- | --- | --- |

FIG. 7

SYSTEMS AND METHODS FOR WIRELESS CONTROL OF NONINVASIVE ELECTROTHERAPY

CROSS REFERENCE TO RELATED APPLICATIONS

This application is a divisional of U.S. application Ser. No. 16/126,822, filed Sep. 10 2018, which is continuation of U.S. application Ser. No. 15/495,532, filed Apr. 24, 2017, which is a divisional of U.S. application Ser. No. 14/191, 146, filed Feb. 26, 2014, now U.S. Pat. No. 9,630,013 on Apr. 25, 2017, which claims priority under 35 U.S.C. § 119(e) to U.S. Provisional Patent Application No. 61/771, 636, filed Mar. 1, 2013, entitled "SYSTEMS AND METHODS FOR WIRELESS CONTROL OF NONINVASIVE ELECTROTHERAPY." The disclosures of all of the above-referenced prior applications, publications, and patents are considered part of the disclosure of this application, and are incorporated by reference herein in their entirety.

BACKGROUND

Technological Field

This application relates generally to systems and methods for conducting electrotherapy.

Description of the Related Art

Energy-based therapeutic devices rely on the application of energy to an external region of a patient's body in order to provide localized treatment or relief to a condition affecting the region. Treatment can be provided using any combination of one or more of a number of energy sources, including low-voltage electricity, magnetic waves, radio waves, shockwaves, microwaves, radiofrequency, laser, heat waves, ultrasound, light waves, and the like. The energy is delivered to a desired region of the patient via externally applied energy transmission member or node (e.g., electrodes, pads, transducers, or patches) attached to the device. For example, electrotherapy includes the application of electrical or electromagnetic stimulation to a particular part of the body for medical purposes. Electrotherapy treatment is widely used by doctors, therapists, athletes, trainers, and coaches for a variety of medical applications, including muscle stimulation, neurological diseases, pain management, treatment of neuromuscular dysfunction, improving the range of joint mobility, tissue repair, treatment for acute and chronic edema, improving peripheral blood flow, iontophoresis, preventing thrombosis post-surgery, and urine and fecal incontinence among other ailments. Electrotherapy treatments generally involve the use of an electrostimulation device to generate electrical pulses which are delivered to the treatment site via electrodes placed in close proximity to the site. The electrodes are available in an assortment of practical and useful shapes and sizes, and may be applied to the body by being planted on the surface of the skin, just beneath the skin, or deep into tissue, depending on the nature of the injury or the particular treatment sought.

People often use electrical stimulation devices such as electrotherapy devices, during or after exercise for one or both of rehabilitative and prophylactic treatment. Transcutaneous electrical nerve stimulation ("TENS") and other electro-stimulation ("electrostim") systems use electrodes and controllers which are connected and operated by wired connections. Wireless devices have also been developed. However, available wireless devices operate with stand-alone controllers that have no other utility or functionality for the user. Thus, a user who wants to wear a wireless TENS unit when jogging, would need to carry a separate mobile device if he or she wanted to retain telephone, email, web and other wireless functionality. As people become more reliant on "smartphones" and other mobile devices such as tablet computers, it becomes increasingly cumbersome and unworkable to carry multiple devices when exercising. Furthermore, many electrostim units are bulky and cumbersome. These units are difficult to place under clothing or in certain areas on the body, especially when wearing these units while exercising, lying down, or sleeping, or in other environments where the units are difficult to manipulate or where the settings can get bumped and inadvertently changed.

SUMMARY

The devices of the present invention have several features, no single one of which is solely responsible for its desirable attributes. Without limiting the scope of this invention as expressed by the claims which follow, its more prominent features will now be discussed briefly. After considering this discussion, and particularly after reading the section entitled "Detailed Description," one will understand how the features of this invention provide several advantages over current designs.

Disclosed herein are improved devices, systems, and methods for providing non-invasive electrotherapy and/or electrical stimulation through a communications platform that is controlled by a computing device or computing circuitry. The communications platform includes wireless communication circuitry, hard-wired circuitry, or a combination of both, configured to communicate with and be controlled by a computing device or computing circuitry. In general, the devices are positioned non-invasively on a patient's body (e.g., on the leg, arm, back, or abdomen) without penetrating the patient's tissues and are configurable in various stimulation modes (discussed further below) to send electrical signals into the patient's tissues beneath the surface to treat muscle or back pain, relieve swelling, enhance blood flow, or other non-invasive uses. The devices and systems include electrotherapy and/or electrical stimulation devices with electronics and one or more conductive layers configured with communication circuitry and pulse generation circuitry. In some aspects, electrotherapy devices described herein are configured to provide iontophoresis therapy in addition to electrotherapy and/or electrical stimulation.

In certain embodiments, a noninvasive electrotherapy device includes a nonconductive top layer; a first electronics layer that has a first plurality of conductive contact points; computing circuitry, configured to provide pulse generation control signals or pulse generation data; pulse generation circuitry, configured to deliver electrical waveforms according to instructions encoded in the pulse generation control signals, in electrical communication with the first plurality of conductive contact points; and a conductive layer comprising a plurality of conductive zones. The computing circuitry can be hardwired onto the electrotherapy device, or housed in a separate computer.

In certain implementations, a device for noninvasive electrotherapy includes a plurality of electronics layers (e.g., formed in spatial layers, located in different spatial areas of the device, or located proximate to each other but having electrically isolated circuits) that can each receive signals and provide pulse generation control signals. For example, a first electronics layer includes one or a plurality of conductive contact points and pulse generation circuitry (for example, wireless communication circuitry), in electrical communication with the conductive contact points; and a second electronics layer comprising computing circuitry configured to provide pulse generation control signals (for example through a wire that connects to a computing device). Either one or both of the electronics layers can generate pulse generation electrical waveform signals and deliver them to one or more conductive zones, for transmission to the patient. The wireless and wire-based circuitry can be selectively activated and deactivated, such that one (e.g., the wire-based circuitry) can be inactive while the other is active.

In certain embodiments, the devices have layers of material that contain the circuitry. In certain embodiments, a device includes a nonconductive top layer, and an electronics layer that has communication circuitry (e.g., wireless communication circuitry, wire-based communication circuitry, and/or circuitry hard-wired into the device itself) for receiving pulse generation control signals from a computing device. The embodiments also include pulse generation circuitry, configured to deliver electrical waveforms according to instructions encoded in the pulse generation control signals, in electrical communication with a first plurality of conductive contact points in the electronics layer. A conductive layer is also included, having a plurality of conductive zones, disposed beneath the nonconductive top layer and the electronics layer. The conductive layer also has a corresponding second plurality of conductive contact points in electrical contact with the first plurality of conductive contact points of the electronics layer. In some implementations, each of two or more of the first conductive contact points is in contact or other communication with the second plurality of conductive contact points, preferably with respective ones of the second conductive contact points. The device is configured to provide electrical stimulation through the conductive zones, using stimulation waveforms selected so as to provide desired stimulation modes. Such modes may include, for example, high and low rate Transcutaneous Electrical Nerve Stimulation (TENS) for pain relief, Neuromuscular Electrical Stimulation (LAMES) for muscle contraction and rehabilitation, Interferential Stimulation (IF) for deep tissue pain management, Pre-Modulated (PreMod) Interferential Stimulation, and High Volt Pulsed DC (HVPDC) galvanic stimulation and Low Volt Pulsed DC (LVPDC) for wound healing regimens.

A nonconductive intermediate layer may be disposed between the electronics layer and the conductive layer. The nonconductive intermediate layer may be sized and shaped so that its diameter is greater than an outer diameter of the conductive layer. In some implementations, an outer perimeter portion of the nonconductive intermediate layer overlays and extends radially further than the outer diameter of the conductive layer. The nonconductive intermediate layer may be plastic or other appropriate material, and is secured to the nonconductive top layer by adhesive or other suitable material. In certain implementations, the second plurality of conductive contact points is in electrical communication with the first plurality of conductive contact points. In certain implementations, the second plurality of conductive contact points is in alignment with the first plurality of conductive contact points. The contact points can be physical contact points and in some implementations are formed via a corresponding plurality of puncture connections through the nonconductive intermediate layer and optionally through one or more electronics layers.

In certain embodiments, circuitry in the electronics layer is substantially surrounded by an adhesive interface disposed in an outer perimeter portion of the nonconductive intermediate layer. The adhesive interface can secure the nonconductive top layer to the nonconductive intermediate layer, such that the circuitry in the electronics layer is enclosed between the nonconductive top layer and the nonconductive intermediate layer in the assembled device. The conductive layer may include a conductive film secured to the nonconductive intermediate layer. The conductive layer can be fixedly secured to the nonconductive intermediate layer, for example by adhesive or other suitable material.

A gel layer may be disposed beneath the conductive layer. In certain implementations, the gel layer includes a plurality of gel zones disposed beneath the corresponding plurality of conductive zones. The plurality of gel zones can be spaced apart from each other and may be separated by an insulating material. The gel layer may be separable from the conductive layer. The gel layer may also be separate from the conductive layer, wherein the gel layer is overlaid with a removable cover sheet. In certain applications, the perimeter dimensions of the gel layer approximately match the perimeter dimensions of the conductive layer when the cover sheet is removed and the gel layer is adhered to the conductive layer. The gel layer may be disposed on a patient's tissue prior to adhesion between the conductive layer and the gel layer. There may also be applications where no gel layer is disposed below the conductive layer. In such cases, the gel may be provided in its own separate container. The gel container may be configured as a roll-on structure or a spray structure, or any other suitable delivery structure. Crosslinkable gels are also contemplated, for example the gel in the container may crosslink in the presence of light of a predetermined wavelength. In certain embodiments, the electrotherapy device includes an integral light source that emits light of the predetermined wavelength.

The conductive zones are also configured for use in the communications platform. In one embodiment, the conductive zones are spaced apart from each other. In certain embodiments, at least one of the plurality of conductive zones is ring-shaped. In certain designs, the plurality of conductive zones includes a ring-shaped conductive zone and a non-ring-shaped conductive zone disposed within an interior area defined by the ring-shaped conductive zone. The plurality of conductive zones may be arranged concentrically or in other suitable configurations. In certain approaches, the nonconductive top layer has an elongated shape and at least two conductive zones are disposed in proximity to opposite ends of the elongated shape. In certain embodiments, a first terminal of the pulse generation circuitry is in electrical contact with a first conductive zone and a second terminal of the pulse generation circuitry is in electrical contact with a second conductive zone.

The wireless communication circuitry can include communication circuitry that may include a wireless personal area network (WPAN) transceiver, such as a ZigBee™ transceiver or other Bluetooth™ transceiver.

In certain embodiments, the devices and systems include a flexible power source disposed below the nonconductive top layer. The flexible power source may be configured as a flexible battery and may be rechargeable. In certain implementations, the battery or other power source is disposed below the nonconductive top layer and capacitive charging circuitry that is in electrical communication with the power source.

The electronics layer may be disposed at least partially beneath the nonconductive top layer, but it may alternatively be disposed at least partially above the nonconductive top layer. At least some components of the electronics layer may be housed within a shell or other housing disposed at least partially above the nonconductive top layer. The shell or housing may include a nonconductive housing. In some aspects, a nonconductive housing is secured to a top surface of the nonconductive top layer. In some implementations, the nonconductive housing includes a flange, and the flange is disposed adjacent to the nonconductive top layer. The flange may also extend around the perimeter of the nonconductive housing. The flange may also be disposed below the nonconductive top layer, while a top portion of the nonconductive housing extends through an aperture in the nonconductive top layer. The nonconductive housing may be shaped asymmetrically. The nonconductive housing can be a formed of a stiff material or a flexible material. The nonconductive housing may be formed of rubber, formable polymer, Styrene foam, or other suitable material. In certain designs, the area of the nonconductive top layer is greater than the area of the conductive layer. In some designs, the nonconductive housing can be large enough to enclose the electrotherapy device as well as at least one remote electrode electrically connected to the device through lead wires.

In certain embodiments, the devices and systems include at least one user-depressible button disposed within the nonconductive housing. Each user-depressible button is coupled to circuitry for receiving a user input command. In some implementations, the devices and systems include a first user-depressible button disposed at one end of the nonconductive shell and a second user-depressible button disposed at another end of the nonconductive shell. In this example, the first user-depressible button is coupled to circuitry for increasing an intensity of electrotherapy and the second user-depressible button is coupled to circuitry for decreasing an intensity of electrotherapy. In certain implementations, the top surfaces of the buttons are positioned below the face of the nonconductive housing, such that the buttons are protected from being pressed unintentionally, especially when the user is exercising, sleeping, or in other environments where the settings can be inadvertently changed. Buttons can also be protected by explicit button guards, or extensions of the nonconductive housing, with their top surfaces higher than the top surfaces of the buttons that they protect. In addition to the above-described buttons, other user-input controls or devices such as switches, dials, knobs, and the like are also fully contemplated by this disclosure.

In certain embodiments, the devices and systems include a display device disposed within the nonconductive housing.

At least one scaffold can be further included to keep the layered electrotherapy device in a desired shape. Such scaffolds can be bent manually into contoured surfaces or shapes to fit and hold the device to a user's body. For example, wire meshes formed of a metal material can be used, as well as stripes and sheets formed by shape-retaining plastic materials. The scaffolds may be disposed within the nonconductive housing, possibly extending across the entire length of the housing. In certain implementations, the scaffolds can also be disposed within the nonconductive top layer. Alternatively, the nonconductive housing itself can be made of shape-retaining materials to serve the purpose of a supporting and contour fitting frame.

Other adaptations may also be made. For example, the pulse generation circuitry may include a current driver configured to drive current from the first conductive zone to the second conductive zone when the first and second conductive zones are placed on a patient's tissue. The electronics layer may further include timer circuitry configured to track the amount of electrotherapy delivered by the pulse generation circuitry, the number of times the electrotherapy is delivered, number of times or duration of the times the device has been "turned on," or other usage device. The timer circuitry may include a memory device for storing at least one of a time duration of delivered electrotherapy, a pulse count of delivered electrotherapy, and a number of delivered electrotherapy sessions. In certain implementations, the wireless communication circuitry includes a processor configured to encode, into a signal for wireless transmission to the computing device, at least one of the stored time duration of delivered electrotherapy, the stored pulse count of delivered electrotherapy, and the stored number of delivered electrotherapy sessions. The electronics layer may also include a memory device in which one or more electrotherapy programs are stored. The wireless communication circuitry may also include a processor configured to decode one or more electrotherapy programs from the received pulse generation control signals and store the one or more decoded electrotherapy programs in the memory device.

In another aspect, the non-invasive electrotherapy devices can be configured as a non-invasive electrical stimulation patch, having a nonconductive housing and one or a plurality of conductive zones. An electronics layer is disposed within the housing and includes communication circuitry configured to receive pulse generation control signals from a computing device. The electronics layer also includes pulse generation circuitry, configured to deliver electrical waveforms according to instructions encoded in the pulse generation control signals. The electrical stimulation patch can include any of the components and operational modes indicated generally for the non-invasive electrical therapy devices. For example, the patch can be structured with various conductive zones and contact points. The patch's communication circuitry may include first communication circuitry having a wireless transceiver configured to wirelessly receive a first set of pulse generation control signals from the computing device. It may also include non-wireless communication circuitry. For example, the patch may have a hard-wire connection capability for connecting to an external computing device. For example, the patch may include a wire connection port configured to receive a wire connecting to the computing device, and second communication circuitry configured to receive a second set of pulse generation control signals from the computing device through the wire. A switch may be included in the patch that deactivates a respective one of the first and second communication circuitry when the other of the first and second communication circuitry is active. The patch electronics can be configured so that the pulse generation control signals are derived from pulse generation control signals received from the computing device through the wireless transceiver, or through the wired connection.

One or a plurality of conductive zones may be disposed beneath the nonconductive top layer and the electronics layer, wherein the conductive layer has a corresponding second plurality of conductive contact points in electrical contact with the first plurality of conductive contacts points. One or more nonconductive intermediate layers may be used, for example being disposed between the electronics layer and the conductive zone. Housings and scaffold structures may also be used to help protect and shape the patch so it fits as optimally as possible to the patient.

In certain applications, the computing device includes a cellular telephone device such as an Android device or a "smartphone." The computing device may also include a portable media player, a personal digital assistant, a tablet computer, or an Internet access device. In certain implementations, the computing device is configured with computing and wireless electrotherapy components, as discussed above, but also provides "smartphone" services, such as wireless telephone, Internet, text message and other such techniques. In some adaptations, the electrical stimulation signals are sent at the same time audio, video, texting, or other communication signals are being processed and delivered by the computing device. In certain applications, the computing device transmits pulse generation control signals to the wireless communication circuitry after receiving a user command input on a touch pad interface of the computing device. The user command may include a purchase request for an electrotherapy program, a request for consultation on therapy regimens, or other desired information or instructions. The user command may include, for instance, an electrotherapy start command.

The electrotherapy devices disclosed herein may be configured for wired communication with computing devices, in addition to or instead of wireless communication.

Moreover, electrotherapy devices disclosed herein, including electrical stimulation patches, may be combined with the computing device or circuitry from which pulse generation control signals are received, forming a non-invasive electrotherapy system. In this system, the electrotherapy device may be configured for wired communication with the computing device, in addition to or instead of wireless communication. In some implementations, the system is configured with circuitry to conduct both wired and wireless communication.

In another aspect provided for non-invasive electrotherapy devices and an electrical stimulation devices described herein, the computing device is implemented as computing circuitry within the device itself. In such aspects, the electrotherapy or electrical stimulation device can be cordless, because the device is controlled entirely with on-board circuitry and on-device user inputs. The computing circuitry can be implemented as part of the first electronics layer, or as a second electronics layer electrically connected to the first electronics layer. In certain embodiments, the electrotherapy device further includes a display device, electrically connected to the computing circuitry. The display device can have a touchpad interface configured to receive user command inputs. In certain embodiments, at least one user-depressible button or other similar controls (e.g., a switch) are included to receive user command inputs. In certain embodiments, the computing circuitry is implemented within the device, but the device is also adapted to interface with an external computing device by a wireless or wired connection, or both. For example, the non-invasive electrotherapy device can be connected by wire to another computing device, such as a mobile "smartphone," and the electrotherapy device (including, for example, programming of stimulation parameters and delivery of stimulation signals) can be controlled by the smartphone through the wired connection. Various methods and systems can be configured and applied using embodiments disclosed herein or variations thereof.

A device for noninvasive electrotherapy is provided in one embodiment. The device includes a nonconductive top layer, an electronics layer, and a conductive layer. The electronics layer may be positioned between the nonconductive top layer and the conductive layer. The electronics layer includes a first plurality of conductive contact points, wireless communication circuitry, and pulse generation circuitry. The wireless communication circuitry is configured to receive pulse generation control signals transmitted from a computing device. The pulse generation circuitry is configured to deliver electrical waveforms according to instructions encoded in the pulse generation control signals. The pulse generation circuitry is in electrical communication with the first plurality of conductive contact points. The conductive layer includes a plurality of conductive zones. The conductive layer also includes a second plurality of conductive contact points in electrical contact with the first plurality of conductive contacts points and the plurality of conductive zones. The plurality of conductive zones is configured to deliver electrical waveforms received from the pulse generation circuitry through the first plurality of conductive contact points and the second plurality of conductive contact points. In another aspect, a device for noninvasive electrical stimulation includes the above features described with reference to a device for noninvasive electrotherapy. The device for noninvasive electrical stimulation may be in the form of a patch.

A method of performing non-invasive electrical stimulation is provided in another embodiment. The method includes providing a non-invasive electrical stimulation device, the device including pulse generation circuitry in electrical communication with communication circuitry. The communication circuitry is configured to receive and process pulse generation control signals. The method also includes wirelessly transmitting pulse generation control signals from a computing device to the communication circuitry. The method also includes delivering electrical stimulation waveforms according to instructions encoded in the pulse generation control signals.

BRIEF DESCRIPTION OF THE DRAWINGS

These and other features, aspects, and advantages of the present invention will now be described in connection with embodiments of the present invention, in reference to the accompanying drawings. The illustrated embodiments, however, are merely examples and are not intended to limit the invention.

FIG. 6C illustrates example stimulation waveform shapes stored in a data structure of an electrotherapy device for use in a non-invasive electrotherapy regimen.

FIG. 7 illustrates a data structure for storing usage data in a memory of an electrotherapy device according to one embodiment.

DETAILED DESCRIPTION

Any feature or combination of features described herein are included within the scope of the present disclosure provided that the features included in any such combination are not mutually inconsistent as will be apparent from the context, this description, and the knowledge of one skilled in the art. In addition, any feature or combination of features may be specifically excluded from any embodiment of the present disclosure. For purposes of summarizing the present disclosure, certain aspects, advantages, and novel features of the present disclosure are described herein. Of course, it is to be understood that not necessarily all such aspects, advantages, or features will be present in any particular embodiment of the present disclosure.

In reference to the disclosure herein, for purposes of convenience and clarity only, directional terms, such as, top, bottom, left, right, up, down, upper, lower, over, above, below, beneath, rear, and front, may be used. Such directional terms should not be construed to limit the scope of the invention in any manner. It is to be understood that embodiments presented herein are by way of example and not by way of limitation. The intent of the following detailed description, although discussing exemplary embodiments, is to be construed to cover all modifications, alternatives, and equivalents of the embodiments as may fall within the spirit and scope of the invention.

Described herein are devices, systems, and methods for noninvasive electrotherapy in which an electrotherapy device includes communication circuitry for receiving pulse generation control signals from computing circuitry (such as a computing device), and pulse generation circuitry for delivering electrical waveforms according to instructions encoded in the pulse generation control signals. In certain implementations, the noninvasive electrotherapy device described herein can be configured to provide iontophoresis therapy in addition to electrotherapy and/or electrical stimulation.

Figure 1A:
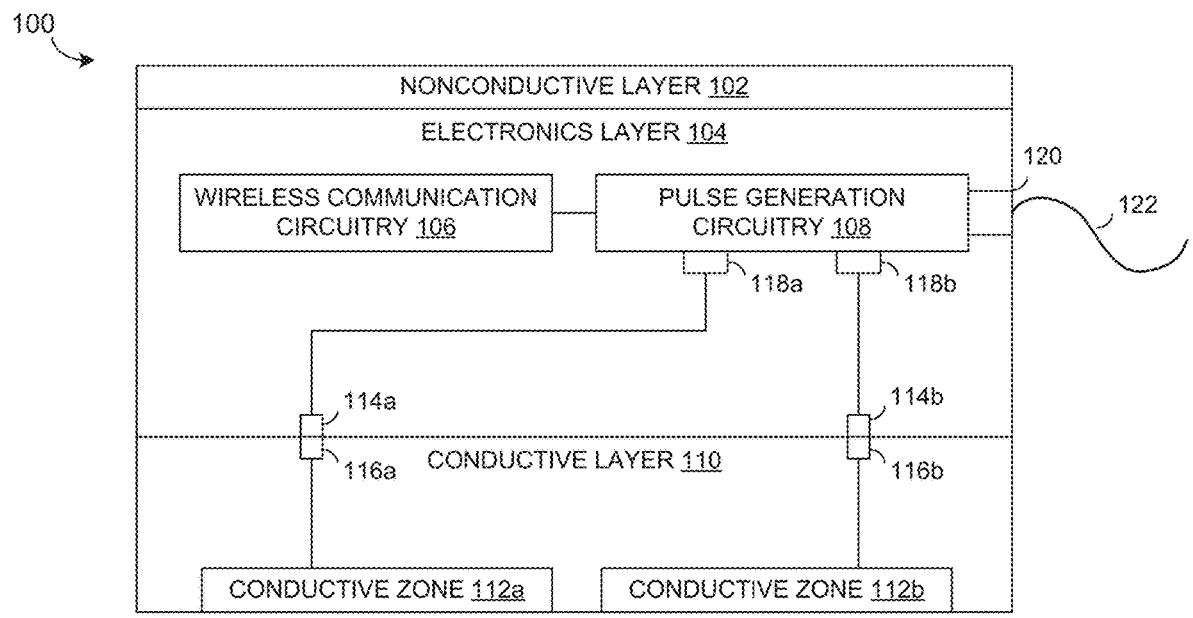
FIG. 1A is a cross-sectional view of an embodiment of an electrotherapy device.

FIG. 1A is a cross-sectional view of an electrotherapy device 100. The device can be positioned non-invasively on a patient's body part (e.g., on the leg, arm, back, abdomen, or other body part) without penetrating the patient's tissues. The device is configurable in various stimulation modes (discussed further below) to send electrical signals into the patient's tissues beneath the surface of the body part to treat muscle or back pain, relieve swelling, enhance blood flow, facilitate wound healing, or other non-invasive uses. In one embodiment, the electrotherapy device 100 is wirelessly controlled and includes a nonconductive top layer 102, an electronics layer 104, and a conductive layer 110. The electronics layer 104 includes wireless communication circuitry 106 and pulse generation circuitry 108. The wireless communication circuitry 106 receives pulse generation control signals or pulse generation data from a computing device (not shown). Pulse generation control signals convey information relevant to pulse generation. They may include, but are not limited to, control information for the pulse generation circuitry 108, stimulation parameters such as voltage levels and frequencies, or stimulation programs (e.g., pre-defined sets of stimulation parameters), and the like. Pulse generation control signals are considered a type of pulse generation data, which may further include information such as new waveform definitions and reference voltage levels. The computing device may include a personal communication device, such as a cellular telephone device or an internet access device. For example, the computing device may be an iPhone device, a Blackberry device, an Android smartphone, an iPad, or any other personal communication device. The computing device may include a media playing device, such as an MP3 player or video player. The computing device may use an RF-based protocol, and may use a proprietary or public communication protocol. In some implementations, the wireless protocol is a Bluetooth™, Zigbee™, or WiFi protocol (e.g., IEEE 802.11 standard).

Figure 1B:
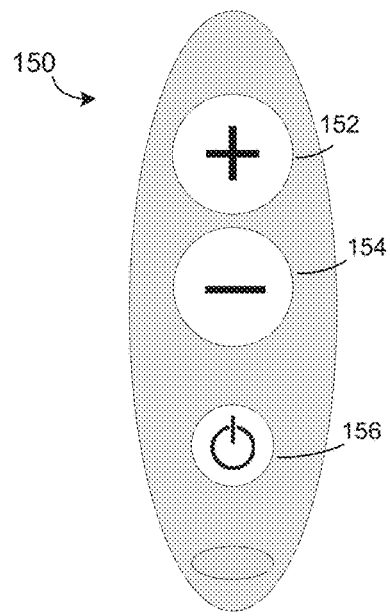
FIG. 1B is a plan view of a key fob for controlling the electrotherapy device of FIG. 1A.

In some implementations the computing device may include a wireless key fob, such as key fob 150 of FIG. 1B. Key fob 150 may be used to wirelessly control electrotherapy device 100. In this implementation, key fob 150 includes three user-depressible buttons 152, 154, and 156. As shown in FIG. 1B, a power button 156 may be pressed by a user or clinician to activate the electrotherapy device 100 to initiate (and possibly to terminate) an electrotherapy program. The buttons 152 and 154 are marked with "+" and "−" symbols, respectively, to indicate that a user may use those buttons to adjust up and down, respectively, the intensity of the electrotherapy provided by the electrotherapy device 100 (e.g., changing the amplitude or frequency of a generated stimulation current). Additional user interfaces that may be implemented instead of or in addition to the buttons 152, 154, and 156 are described in Mueller et al., U.S. Patent Application Publication No. 2010/0042180, incorporated by reference herein in its entirety.

The pulse generation circuitry 108 of the electrotherapy device 100 delivers electrical waveforms, according to instructions encoded in the wireless pulse generation control signals, through first and second terminals 118a and 118b that are in electrical communication with conductive contact points 114a and 114b, respectively. The conductive layer 110 is disposed beneath the nonconductive top layer 102 and the electronics layer 104, and includes two conductive contact points 116a and 116b that are in alignment and in electrical contact with the conductive contact points 114a and 114b of the electronics layer 104. The conductive contact points 116a and 116b of the conductive layer 110 are in electrical contact with corresponding conductive zones 112a and 112b. In use, the electrotherapy device is positioned so the conductive layer 110 is against a user's tissue. A current driver (not shown) included in the pulse generation circuitry 108 can drive electrical current from the first terminal 118a of the pulse generation circuitry 108, through the conductive contact point 114a, through the conductive contact point 116a, through the conductive zone 112a, into the user's tissue, then back to the second terminal 118b of the pulse generation circuitry 108 through the conductive zone 112b, the conductive contact point 116b, and the conductive contact point 114b.

In some implementations, pulse generation circuitry 108 delivers electrical waveforms, according to instructions encoded in the wireless pulse generation control signals, through an external terminal 120. One or more lead wires 122 may be connected to external terminal 120 to carry an electrical signal to one or more remote electrodes (not shown). For example, lead wire 122 may connect to two remote electrodes, where a first remote electrode drives electrical current into the user's tissue, and a second remote electrode returns current through lead wire 122 and back to the pulse generation circuitry 108. The electrotherapy device 100 controls delivery of electrical signals to the one or more remote electrodes, for example, using wireless communication circuitry 106. Remote electrodes can allow for added angular positioning and placement of the electrodes on remote areas of the body where it is difficult to place conductive zones 112a and 112b. For example, electrotherapy device 100 may be placed on the user's thigh while one or more remote electrodes are placed on the user's knee.

Figure 1C:
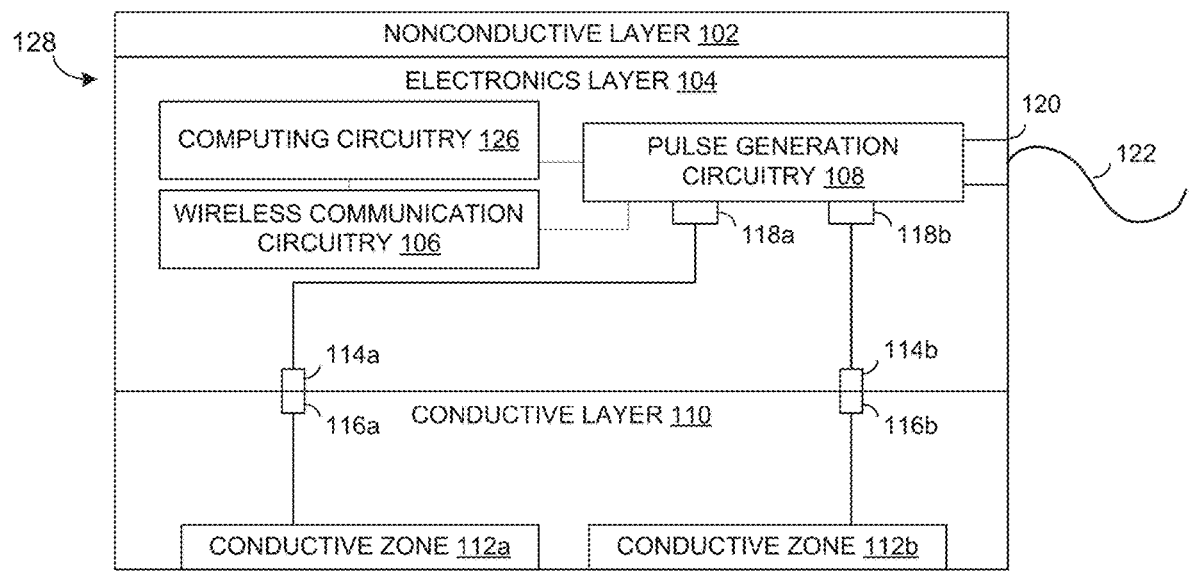
FIG. 1C is a cross-sectional view of an embodiment of an electrotherapy device including on-board computing circuitry.

FIG. 1C is a cross-sectional view of an electrotherapy device 128 according to one embodiment of the present disclosure. In this implementation, electrotherapy device 128 includes computing circuitry 126 as part of the electronics layer. This computing circuitry 126 is electrically connected to the wireless communication circuitry 106 and the pulse generation circuitry 108. In some implementations, the computing circuitry 126 can provide pulse generation control signals, according to which the pulse generation circuitry 108 deliver electrical waveforms to the conductive zones 112a and 112b. In this embodiment shown in FIG. 1C, the electrotherapy device 128 is also wirelessly controlled by a computing device (not shown), through bidirectional data exchanges across the wireless communication circuitry 106. This computing device can wirelessly transmit to the electrotherapy device 128 a set of pulse generation control signals. The computing device may be a personal communication device (e.g. cellular telephone), a media playing device (e.g. MP3 player), a personal digital assistant, a tablet computer (e.g., iPad), or a wireless key fob (e.g., key fob 150 of FIG. 1B). In some implementations, the wireless communication circuitry 106 is disabled, or excluded during assembly, such that the computing circuitry 126 serves as the sole controller and the sole pulse generation control signal provider for the electrotherapy device 128. In other implementations, the pulse generation control signal from the computing device may be stored, or used by the on-board computing circuitry 126 directly or indirectly in generating pulse generation control signals to be delivered by the computing circuitry 126. In addition, the computing circuitry 126 may be configured to control the delivery of electrical signals to the one or more electrodes through lead wires 122 connected to the external terminal 120. Change FIG. 1C to reflect this connection? Although the computing circuitry 126 is illustrated as part of the electronics layer 104 in FIG. 1C, it can also be included in a separate electronics layer, placed anywhere in the stack of layers above the conductive layer 110. Any number of nonconductive intermediate layers may be inserted between the individual layers.

Figure 1D:
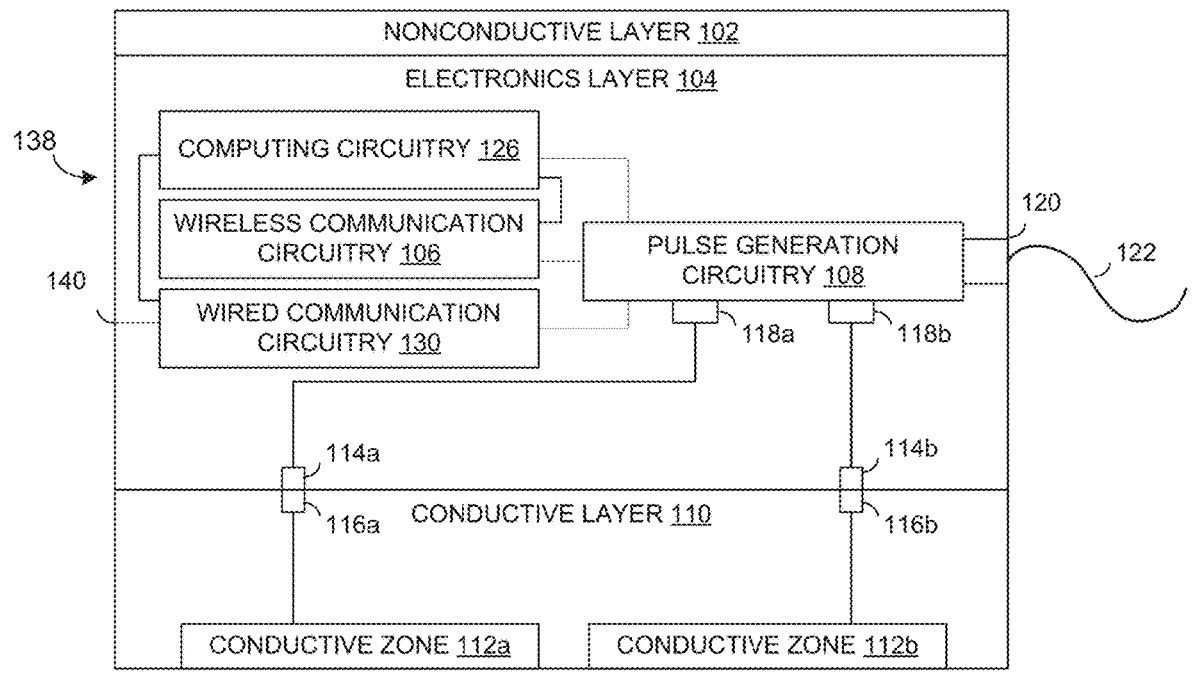
FIG. 1D is a cross-sectional view of an embodiment of an electrotherapy device including on-board computing circuitry and communication circuitry having a wired connection port.

FIG. 1D is a cross-sectional view of an electrotherapy device 138 according to another embodiment of the present disclosure. In this embodiment, the electrotherapy device 138 includes wired communication circuitry 130. This wired communication circuitry 130 is electrically connected to a wire connection port 140, the computing circuitry 126, and the pulse generation circuitry 108. The computing circuitry 126 and the pulse generation circuitry 108 can each exchange bidirectional data with a computing device (not shown) through a wire connection formed across the port 140. This computing device may also be capable of transmitting and receiving data wirelessly to the electrotherapy device. The computing device may transmit different sets of pulse generation controls signals through either or both of the wireless communication circuitry 106 and the wired communication circuitry 130. Either of the wired and wireless connections can serve as a backup communication mode for the other. Pulse generation control signals received at the electronics layer 104 can be processed or stored by the computing circuitry 126, or can be decoded by the pulse generation circuitry 108 for generating electrical waveforms.

Figure 2A:
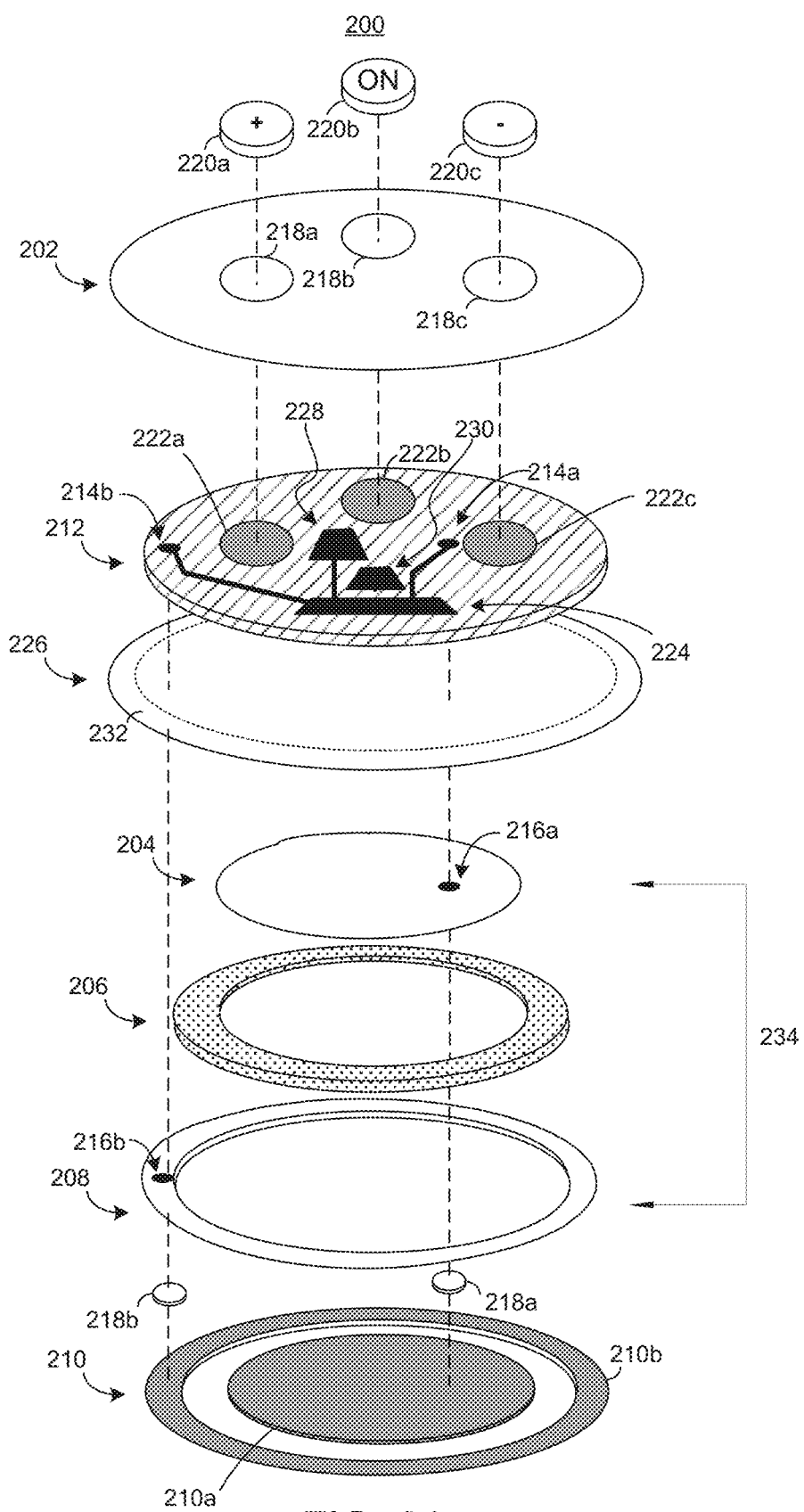
FIG. 2A is an exploded view of another embodiment of an electrotherapy device.

FIG. 2A is an exploded view of an electrotherapy device 200 according to yet another embodiment of the present disclosure. The electrotherapy device 200 includes an electronics layer 212. Like the electrotherapy device 100 of FIG. 1A, the electrotherapy device 200 includes a plurality of conductive zones in a conductive layer 234. In particular, the electrotherapy device 200 includes a nonconductive top layer 202, an electronics layer 212, and a conductive layer 234 having a first conductive zone 204 and a second conductive zone 208. The electrotherapy device 200 also includes an insulating layer 206, shown as a ring with a rim that is positioned between the perimeters of the first conductive zone 204 and the second conductive zone 208. In this embodiment, the electrotherapy device 200 includes a gel layer 210 having a first gel zone 210a and a second gel zone 210b. The electronics layer 212 is disposed between the nonconductive top layer 202 and the conductive layer 234. The electronics layer 212 is relatively thin in this implementation. For example, the electronics layer 212 can have a thickness ranging from about 0.05 inches to about 0.5 inches. In other example embodiments, the electronics layer 212 has a thickness within the range of about 0.05 inches to about 0.1 inches; about 0.1 inches to about 0.3 inches; about 0.06 inches to about 0.5 inches; or about 0.06 inches to about 0.25 inches. Electronics layers 212 with other thicknesses are also possible.

A nonconductive intermediate layer 226 is disposed between the electronics layer 212 and the first conductive zone 204. In some implementations, the nonconductive intermediate layer 226 takes the form of a coating of a nonconductive material (such as a nonconductive plastic) on the bottom surface of the electronics layer 212 or the top surface of the first conductive zone 204. The nonconductive top layer 202 may be made from a nonconductive sheet material (such as PTE) or a non-sheet material (such as styrene foam) and may include an adhesive on its bottom surface, which is used to adhere the nonconductive top layer 202 to the electronics layer 212, the nonconductive intermediate layer 226, or both.

The nonconductive intermediate layer 226 may be sized and shaped so that its diameter is greater than an outer diameter 236 of the conductive layer 234. In some implementations, an outer perimeter portion of the nonconductive intermediate layer 226 overlays and extends radially further than the outer diameter 236 of the conductive layer 234. In the embodiment of FIG. 2A, when the electrotherapy device 200 is assembled, the circuitry in the electronics layer 212 (discussed below) is substantially surrounded by an adhesive interface 232 disposed in an outer perimeter portion of the nonconductive intermediate layer 226. In this implementation, the adhesive interface 232 is provided in a circumferential area between an outer diameter 227a of the nonconductive intermediate layer 226 and a dashed line 227b. The adhesive interface 232 can secure the nonconductive top layer 202 to the nonconductive intermediate layer 226, such that the circuitry in the electronics layer 212 is enclosed between the nonconductive top layer 202 and the nonconductive intermediate layer 226 in the assembled device.

While the diameter of the nonconductive top layer 202 is greater than the diameter of the electronics layer 212 in the example illustrated in FIG. 2A, other configurations are possible. In other implementations, for example, the perimeter of the nonconductive top layer 202 is approximately coextensive with the perimeter of the electronics layer 212, and the nonconductive top layer 202 may be adhesively secured to portions of the electronics layer 212. In some implementations, the electronics layer 212 is disposed only partially beneath the nonconductive top layer 202.

The conductive zones 204 and 208 of the conductive layer 234 can be formed from continuous pieces of aluminum. Other conductive material may be used, such as another metal or a conductive plastic (e.g., a polymer impregnated with carbon). Each of the conductive zones 204 and 208 may be formed by die-cutting a sheet of conductive material, for example. In the embodiment shown in FIG. 2A, the area of the nonconductive intermediate layer 226 is greater than the total conductive area of the conductive layer 234 (including the conductive areas of the conductive zones 204 and 208), the diameter of the nonconductive intermediate layer 226 being larger than the diameter of the conductive layer 234. Thus, the perimeter of the nonconductive intermediate layer 226 extends beyond the perimeter of the conductive layer 234. In some implementations, the area of the nonconductive intermediate layer 226 is approximately equal to the conductive area of the conductive layer 234, with the layers 226, 234 having substantially the same diameter. In some implementations, the conductive zones 204 and 208 of the conductive layer 234 are formed from a conductive film secured to the nonconductive intermediate layer 226. The conductive zones 204 and 208 may be fixedly secured to the nonconductive intermediate layer 226, or they may be removably secured (e.g., via a snap or conductive adhesive connection wire band).

The conductive zone 208 in this embodiment is ring-shaped, while the conductive zone 204 is non-ring-shaped and sized to fit within the interior area of the conductive zone 208. When the electrotherapy device 200 is assembled, the non-ring-shaped conductive zone 204 is disposed within the interior area defined by the ring-shaped conductive zone 208. The conductive zones 204 and 208 are arranged approximately concentrically.

The electronics layer 212 includes circuitry for performing one or more electrotherapy programs. In some implementations, the electronics layer 212 includes a printed circuit board configured with passive and active electrical components to perform a predetermined or programmable electrostimulation protocol. These electrical components may include one or more control microprocessors configured with machine-executable logic to control the conversion of energy from one or more power supplies included in the electronics layer 212 (such as printed or coin cell batteries) into electrostimulation currents that may be driven into a patient's tissue through one or both of the first conductive zone 204 and the second conductive zone 208. The electronics layer 212 includes a power source in this implementation. Embodiments of suitable power sources include, for example, flexible power source 230. In this embodiment, the flexible power source 230 includes a flexible battery disposed below the nonconductive top layer 202. In some implementations, the flexible power source 230 is rechargeable (e.g., using capacitive charging circuitry in electrical communication with the flexible power source 230, as described below with reference to FIGS. 5 and 10). In some implementations, the flexible power source 230 is thin. For example, in one aspect, the thickness of the flexible power source ranges from about 0.015 inches to about 0.25 inches. In certain implementations the range of the thickness is between 0.1 inches to about 0.2 inches; about 0.15 inches to about 0.17 inches; about 0.04 inches to about 0.25 inches; or about 0.04 inches to 0.15 inches. The power source 230 may include, for example, a lithium polymer rechargeable battery.

In one embodiment, the electronics layer 212 includes printed traces of an electrically conductive material on one or more sub-layers (not shown) that connect the circuit components. Among the circuit components included in the electronics layer 212 is wireless communication circuitry 228. The wireless communication circuitry 228 receives wireless pulse generation control signals from a computing device (not shown). Various embodiments of the wireless communication circuitry 228 are discussed below. The electronics layer 212 also includes pulse generation circuitry 224. The pulse generation circuitry 224 generates electrical signals that are transmitted to a patient's tissue via the first conductive zone 204 and the second conductive zone 208.

In the electrotherapy device 200, the electronics layer 212 is in electrical communication with the first conductive zone 204 via a conductive contact point 214a (in the electronics layer 212) and a conductive contact point 216a (in the first conductive zone 204). The conductive contact point 214a is in alignment with and physically contacts the conductive contact point 216a when the electrotherapy device 200 is assembled.

In certain approaches, these conductive contact points 214a and 216a are electrically connected by a puncture technique, in which the conductive contact point 214a of the electronics layer 212 is aligned with and positioned adjacent to the conductive contact point 216a of the first conductive zone 204, and the electronics layer 212, the first conductive zone 204, and the nonconductive intermediate layer 226 are all punctured at the conductive contact points 214a and 216a to form an electrical connection between the conductive materials included in the electronics layer 212 and the first conductive zone 204. In some implementations, the puncture connections are formed by pushing a pin, rod, or other rigid member through a conductive portion (e.g., conductive contact points 214, 216 discussed below) of the electronics layer 212 (and nonconductive intermediate layers) to deform the conductive portion and form a hole surrounded by protrusions of the conductive material extending away from the electronics layer 212. In some implementations, these protrusions are jagged and irregular, while in other implementations, the body of the conductive layer is pre-scored or otherwise prepared so that the protrusions are more regularly spaced and sized. When the electronics layer 212 is separated from the first conductive zone 204 by the nonconductive intermediate layer 226, the protrusions extend through the nonconductive intermediate layer 226 and can be bent to fold back against the first conductive zone 204 to form an electrical connection between the conductive portion of the electronics layer 212 and the first conductive zone 204. In some implementations, the electronics layer 212, the nonconductive intermediate layer 226, and the first conductive zone 204 are stacked, and the puncturing operation is applied to the entire stack.

Because the electronics layer 212 is separated from the first conductive zone 204 at all points (other than the puncture locations) by the nonconductive intermediate layer 226, the puncture connection between the conductive contact points 214a and 216a will allow electrical signals generated by an appropriate channel of the pulse generation circuitry 224 (e.g., a first channel) to flow to the first conductive zone 204 without short-circuiting the remaining components in the electronics layer 212. Although FIG. 2A only shows one conductive contact point between the electronics layer 212 and the first conductive zone 204 (at points 214a and 216a), any number of conductive contact points may be used.

As further shown in FIG. 2A, the gel layer 210 is disposed beneath the conductive layer 234. Any suitable gels, such as conductive hydrogels, may be used in the gel layer 210. The gel layer 210 includes two gel zones 210a and 210b disposed beneath the corresponding conductive zones 204 and 208. As shown, the gel zones 210a and 210b are spaced apart from each other. In some implementations, an insulating material (such as the insulating layer 206) separates the gel zones 204 and 208.

The electrotherapy device 200 according to this embodiment also includes a nonconductive element 218a positioned below the conductive contact point 216a. The nonconductive element 218a is formed from an insulating material, such as a dielectric polymer, and has perimeter dimensions that are equal to or greater than the footprint of the conductive contact point 216a. In use, current from an electrotherapy device passes from the pulse generation circuitry 224 to the conductive contact point 214a, and then to the first conductive zone 204 via the conductive contact point 216a. The current is then distributed to a patient's tissue through the gel zone 210a. The nonconductive element 218a can force current to flow through the gel zone 210a around the nonconductive element 218a, preventing excessive current from taking the path of least resistance from the conductive contact point 216a through the portion of the gel zone 210a directly beneath the conductive contact point 216a to the patient's tissue. This can advantageously prevent a buildup of heat and current (e.g., a "hotspot") directly below the conductive contact point 216a. The electrotherapy device 200 can also include a nonconductive element 218b positioned below the conductive contact point 216b.

One or more sets of similar conductive contact points may be provided. As shown in FIG. 2A, a second set of conductive contact points, 214b and 216b, is configured within the electronics layer 212 and the rim of the second conductive zone 208, respectively. In one aspect, the first set of conductive contact points 214a and 216a are configured to transmit electrical signals to the patient's skin or tissue via the gel zone 210a. The second set of conductive contact points 216b and 214b (via gel zone 210b) may complete the electrical circuit through the patient's skin or tissue, delivering the desired electrotherapy program, as described herein. In another aspect, electrical signals are delivered from the pulse generation circuitry 224 to the patient's skin or tissue through conductive contact points 214b and 216b, the circuit being completed through conductive contact points 216a and 214a. In some embodiments, multiple conductive contact points (e.g., 214a, 216a, 214b, 216b) may be employed providing multiple electrical paths for the delivery of a selected electrotherapy program to the patient's skin or tissue.

In one aspect, electrical signals generated on a second channel of the pulse generation circuitry 224 are transmitted to the second conductive zone 208 via the conductive contact points 214b and 216b. The conductive contact points 214b and 216b can be connected using the puncture technique described above.

In the embodiment of FIG. 2A, when the electrotherapy device 200 is assembled, it has a minimal thickness and thus retains a very low profile. Due to the minimal thickness of each corresponding layer, the electrotherapy device may have an assembled thickness of less than about 0.5 inches in one aspect. In certain implementations, the assembled thickness is less than about 0.25 inches. In other implementations, the assembled thickness is less than about 0.1 inches. Other thicknesses of the assembled device are possible. The low profile of embodiments of the electrotherapy device 200 allows for increased ease of use, allowing a user to place the device under clothes or in areas of the body that are difficult to access (e.g., under an arm). The low profile of electrotherapy device 200 may also allow a user to hide the device 200 while wearing it.

Figure 2B:
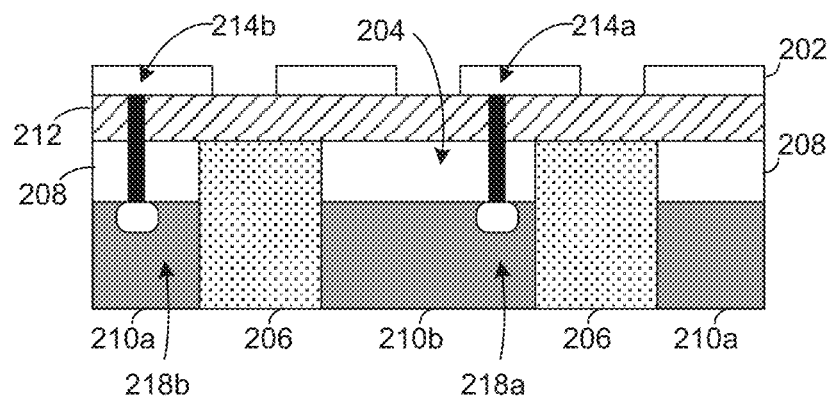
FIG. 2B is a cross-sectional view of the electrotherapy device of FIG. 2A.

FIG. 2B is a cross-sectional view of the electrotherapy device 200 of FIG. 2A. The electrotherapy device illustrated in FIGS. 2A and 2B includes two electrodes (in this aspect, first and second conductive zones 204 and 208) and a single electronics layer (in this aspect, electronics layer 212). However, any number of electrodes and any number of electronics layers, arranged in any desired orientation, may be used (such as any of the electrode systems described herein). When using multiple electrodes, different output channels of the pulse generation circuitry 224 may be directed to different electrodes within the electrotherapy device 200 without the use of bulky wires or the need for hand-soldering. In some implementations, the puncture connections are formed by rotary converting equipment acting on rolls of material that provide the electronics layer 212, the first and second conductive zones 204 and 208, respectively, and the nonconductive intermediate layer 226. Automation of the puncture connection process, as well as other steps in the production of the electrodes and systems described herein, may enable the effective fabrication of previously infeasible structures and may improve the quality of the manufactured items. For example, an automated electrode manufacturing process may be more readily monitored (e.g., using cameras and other sensors) than a manual assembly process, which may enable earlier detection of manufacturing errors thereby preventing unsuitable electrodes from entering the marketplace.

Referring back to FIG. 2A, the electronics layer 212 also includes electrical switches 222a, 222b, and 222c. These electrical switches are components that provide an electrical response to forces exerted on the surface of the switches, and are commonly used in user interface design for registering button presses or other user inputs. As will be described in greater detail below, the switch 222b is a power switch and the switches 222a and 222c are intensity adjustment switches in this embodiment. Three user-depressible buttons or keys 220a, 220b, and 220c are disposed above the electrical switches 222a, 222b, and 222c, respectively, and are aligned with apertures 218a, 218b, and 218c, respectively, in the nonconductive top layer 202. In this aspect, the button 220a is disposed at one end of the nonconductive top layer 202 and the button 220c is disposed at the other end of the nonconductive top layer 202, but other configurations are possible. Although the buttons 220a, 220b, and 220c are shown as approximately equal in size, any one or more of the buttons 220a, 220b, and 220c may be of different sizes, shapes, textures, or other properties that make the buttons 220a, 220b, and 220c visually or tactilely differentiable to a user.

The electrical switches 222a, 222b, and 222c are in electrical communication with a microprocessor or other circuitry of the electronics layer 212 and can be used to initiate or adjust the electrostimulation provided by the electrotherapy device 200. As shown in FIG. 2A, the button 220b is a power button, marked "ON," and may be pressed by a user or clinician to activate the power switch 222b to initiate (and possibly to terminate) an electrotherapy program. The buttons 220a and 220c are marked with "+" and "−" symbols, respectively, to indicate that a user may use those buttons to activate the intensity adjustment switches 222a and 222c to adjust up and down, respectively, the intensity of the electrotherapy provided by the electrotherapy device 200 (e.g., changing the amplitude or frequency of a generated stimulation current). Other symbols are also possible.

Additional user interfaces that may be implemented instead of or in addition to the keys 220a, 220b, and 220c are described in Mueller et al., U.S. Patent Application Publication No. 2010/0042180, incorporated by reference herein in its entirety. In alternative implementations, one or a plurality of switches is used but is activated directly by the user (e.g., through a mechanical switch arm (not shown)) rather than by using buttons. One or more switches can be used to activate and deactivate communication circuitry on an electrotherapy device, for example to deactivate a hard-wired electrical connection between an electrotherapy device and a smartphone when the smartphone is using a wireless connection to control the electrotherapy device.

The pulse generation circuitry 224 included in the electronics layer 212 of the electrotherapy device 200 may be configured to generate electrostimulation waveforms according to one or more electrotherapy programs (e.g., a predefined current or voltage waveform, or a predefined set of stimulation parameters). Different electrotherapy programs can be selected to provide desired electrotherapy stimulation modes. As explained below, examples of such stimulation modes include high and low rate Transcutaneous Electrical Nerve Stimulation (TENS) for pain relief, Neuromuscular Electrical Stimulation (LAMES) for muscle contraction and rehabilitation, Interferential Stimulation (IF) for deep tissue pain management, Pre-Modulated (PreMod) Interferential Stimulation, and High Volt Pulsed DC (HVPDC) galvanic stimulation and Low Volt Pulsed DC (LVPDC) for wound healing regimens. These electrotherapy programs may be stored in a memory (such as an EEPROM) included in the electronics layer 212, or may be encoded into the circuitry (e.g., firmware or software) using logic gates or other circuitry (e.g., an Application Specific Integrated Circuit (ASIC)).

In some implementations, the electrotherapy device 200 is configured to provide a single electrostimulation protocol when the power button 220b is pressed (e.g., a particular TENS therapy or a particular iontophoretic treatment). The single electrostimulation protocol may be directed to treating a particular condition (e.g., pain or muscle tension). In one example, the electrotherapy device 200 is packaged and provided to clinicians and patients as a treatment for the particular condition along with instructions on how to position the electrotherapy device 200 on the patient's body. The electrotherapy device 200 can then be activated and the electrotherapy delivered by depressing the power button 220b. In some implementations, the electrotherapy device 200 can only be used a predetermined number of times before the electrotherapy device 200 will no longer respond to presses of the power button 220b. The number of times that the electrotherapy device 200 has been turned on may be stored in an EEPROM or other memory included in the electronics layer 212, and a microprocessor may be configured to count up or down to a fixed value that represents the maximum number of uses. In some implementations, the electrotherapy programs may provide for electrotherapy over a predetermined period of time (e.g., thirty minutes). The time period may be enforced by timer circuitry included in the electronics layer 212, or by a chemical or other switch in the electronics layer 212. While buttons 220a-b are discussed herein, other controls such as switches, knobs, or other user input devices may also be implemented for the same user-input purpose without departing from the spirit of the disclosure.

Figure 3A:
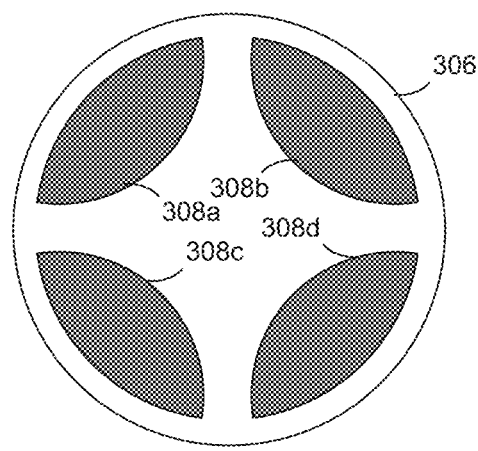
FIGS. 3A and 3B are plan views of different conductive layer configurations that may be used with electrotherapy devices described herein.
Figure 3B:
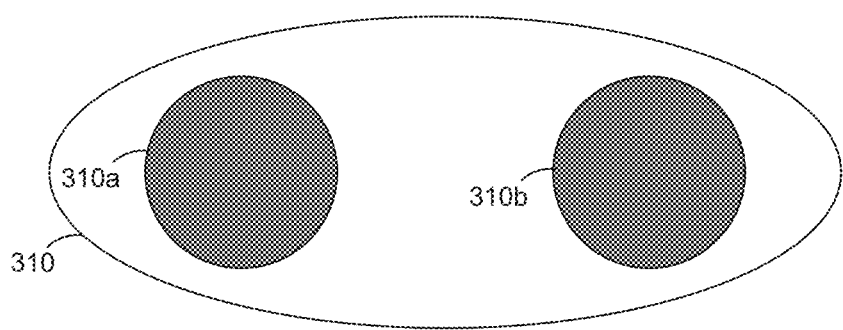

The conductive layer of an electrotherapy device according to the present disclosure may have any number of conductive zones arranged in any number of configurations. FIGS. 3A and 3B are plan views of examples of different conductive layer configurations that may be used with the electrotherapy devices disclosed herein (such as the electrotherapy device 100 of FIG. 1A and the electrotherapy device 200 of FIG. 2). FIG. 3A depicts a nonconductive top layer 306 below which four conductive zones 308a-308d are disposed. In this example, the conductive zones 308a-308d are "eye"-shaped and spaced apart from each other equidistantly about the circumference of the nonconductive intermediate layer 306. In some implementations, an insulating material (such as insulating foam) may be arranged between the conductive zones 308a-308d. In use, current may be directed between different combinations of the conductive zones 308a-308d to achieve a desired stimulation pattern within the user's tissue. For example, current may be directed into the tissue below the conductive zone 308a and directed out of the tissue below the conductive zones 308b-308d. In another example, current may be directed into the tissue below the conductive zones 308a and 308d, and directed out of the tissue below the conductive zones 308b and 308c.

FIG. 3B depicts another example including a nonconductive top layer 310 below which two conductive zones 310a and 310b are disposed. The nonconductive top layer 310 has an elongated shape and the conductive zones 310a and 310b are disposed in proximity to opposite ends of the elongate shape. As shown, the conductive zones 310a and 310b are shaped as circles and have approximately the same dimensions, but in other implementations, the conductive zones 310a and 310b may have different, non-circular shapes of different dimensions. A conductive layer configured as shown in FIG. 3B may be advantageous applied in therapeutic scenarios in which a wide band of electrical stimulation current is desired over an area between the conductive zones 310a and 310b.

As discussed above, a gel layer may be disposed next to the conductive layer of any of the electrotherapy devices described herein. In some implementations, the gel layer includes a plurality of gel zones disposed beneath a corresponding plurality of conductive zones. The plurality of gel zones may be spaced apart from each other, and may be separated by an insulating material.

Figure 4A:
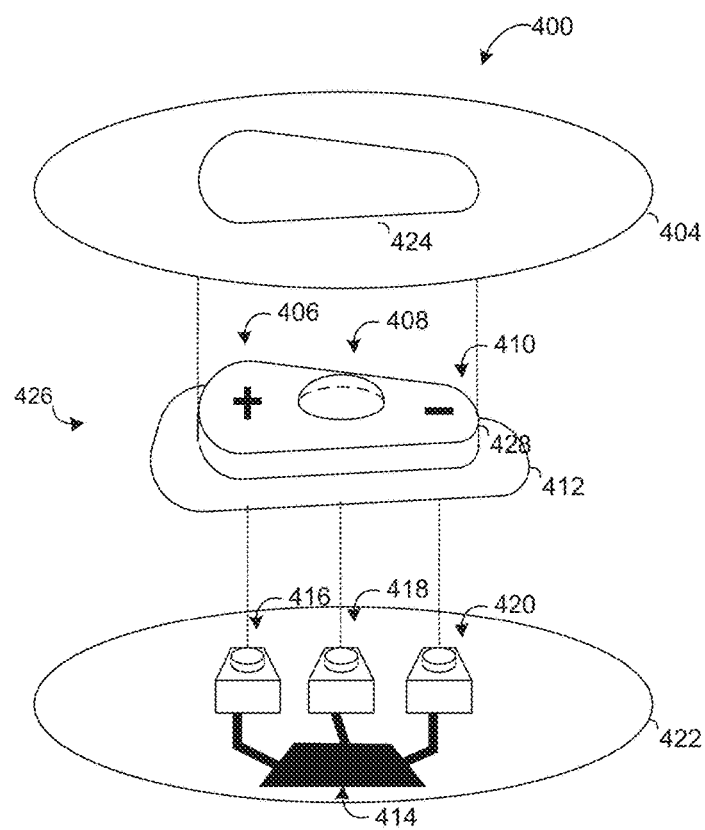
FIG. 4A is an exploded view of an embodiment of an electrotherapy device including a nonconductive housing.

FIG. 4A is an exploded view of an electrotherapy device 400 according to yet another embodiment of the present disclosure. The electrotherapy device 400 includes a nonconductive top layer 404, an electronics layer 422, and a nonconductive housing or shell 426. The housing 426 forms a covering around at least a portion of the electronics components. In this aspect, the nonconductive top layer 404 is made of a sheet material and includes an aperture 424. The aperture 424 is dimensioned to approximately match the dimensions of a top portion 428 of the housing 426 such that, when assembled, the top portion 428 of the housing 426 protrudes through the aperture 424 and extends above the nonconductive top layer 404. The top portion 428 defines an interior chamber into which electronic components of the electronics layer 422 (such as switches 416, 418, and 420) may extend. The housing 426 in this embodiment also includes a flange 412, which extends around the perimeter of the housing 426 and is disposed adjacent to and below the nonconductive top layer 404. When the electrotherapy device 400 is assembled, the switches 416, 418, and 420 are housed within the chamber defined by the top portion 428 of the housing 426 so that the switches 416, 418, and 420 extend above the nonconductive top layer 404 while other components of the electronics layer 422 (such as a flexible power source 414) are disposed beneath the nonconductive top layer 404. In some implementations, the housing 426 does not include a flange, and is secured to a top surface of the nonconductive top layer 404 (e.g., by an adhesive).

In some implementations, the housing 426 is dimensioned to enclose the entire electronics layer 422. The housing 426 may be made of any suitable material, such as, but not limited to, rubber, styrene foam, or other polymer material. In FIG. 4A, the housing 426 is asymmetrically shaped, although it can be symmetric in alternative embodiments. In certain implementations, the housing 426 is flexible, although formable. For example, a rubber housing can be configured so the rubber component is flexible so as to provide ergonomic compatibility with the patient's skin, while at the same time including a scaffold or other stiff material to maintain the housing in its same general shape (e.g., contoured to the patient's appendage or other external body site) during use. Examples of such scaffolding and other stiffening materials are discussed further below.

In the embodiment illustrated in FIG. 4A, the housing 426 also has a first user-depressible button 406 disposed at one end of the housing 426 and a second user-depressible button 410 disposed at another end of the housing 426. In some implementations, such user-depressible buttons are disposed at other positions on the housing 426. The first user-depressible button 406 is positioned to mechanically couple to the switch 416, which is itself coupled to circuitry in the electronics layer 422 for increasing an intensity of electrotherapy. The second user-depressible button 410 is positioned to mechanically couple to the switch 420, which is itself electrically coupled to circuitry in the electronics layer 422 for decreasing an intensity of electrotherapy. The housing 426 also includes a third user-depressible button 408 disposed between the first user-depressible button 406 and the second user-depressible button 410. The third user-depressible button 408 is positioned to mechanically couple to the switch 418, which is itself electrically coupled to circuitry in the electronics layer 422 for changing a powered state of the electrotherapy device, in this example for turning the electrotherapy device 400 on and off. In some implementations, the housing 426 also includes one or more LEDs (not shown) for displaying information about a current state of the electrotherapy device 400. For example, one LED may indicate whether the device is on, while another may indicate whether the power level is low and if recharging is necessary.

Figure 4B:
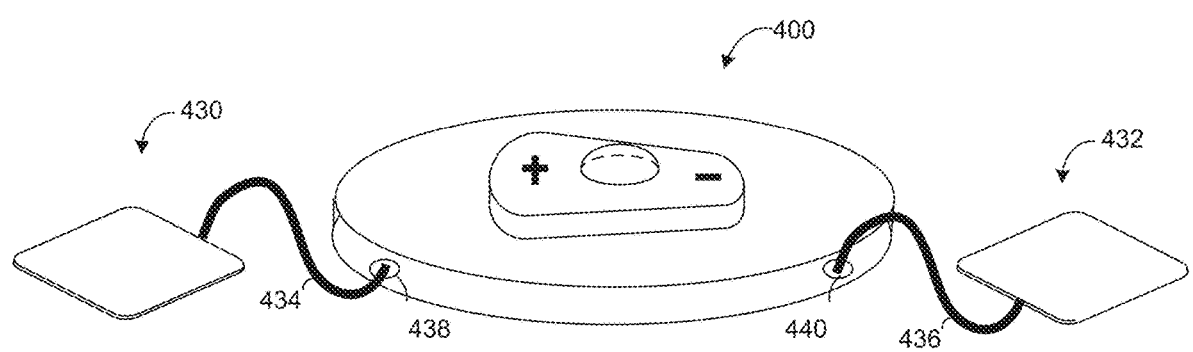
FIG. 4B is a plan view of an embodiment of the electrotherapy device of FIG. 4A including remote electrodes.

FIG. 4B is a plan view of one embodiment of the electrotherapy device 400 having remote electrodes 430 and 432. Remote electrodes 430 and 432 are electrically connected to lead wires 434 and 436. Lead wires 434 and 436 electrically connect to electronics layer 422 of electrotherapy device 400 via ports 438 and 440. While FIG. 4B depicts two remote electrodes, in certain implementations there may be more than two remote electrodes that electrically connect to electrotherapy device 400. In certain implementations, application of an electrical signal to remote electrodes 430 and 432 are controlled by switches 416, 418, and 420. The switches 416, 418, and 420 may be controlled by user input via user-depressible buttons 406, 408, and 410, as described above. In certain embodiments, application of an electrical signal to remote electrodes 430 and 432 is controlled by a computing device including a personal communication device, such as a cellular telephone device or an internet access device. For example, the computing device may be an iPhone device, a Blackberry device, an Android smartphone, or any other personal communication device. The computing device may include a media playing device, such as an MP3 player. In some implementations, the computing device is a personal computer, a server, or a mainframe, for example. In some implementations, the computing device is a portable computing device, such as a tablet device, net book, laptop, mobile telephone, smartphone, or any other such device. In some implementations, the computing device includes multiple computing devices, such as any of those described above. The computing device may include a computer running an operating system, such as but not limited to Windows (Microsoft), Linux, MacOS (Apple), Android (Google), iOS (Cisco Systems), Blackberry OS (Research In Motion), Symbian (Nokia), or Windows Phone (Microsoft) operating systems. The remote electrodes 430 and 432 can allow for added angular placement of the electrodes on areas of body.

Figure 4C:
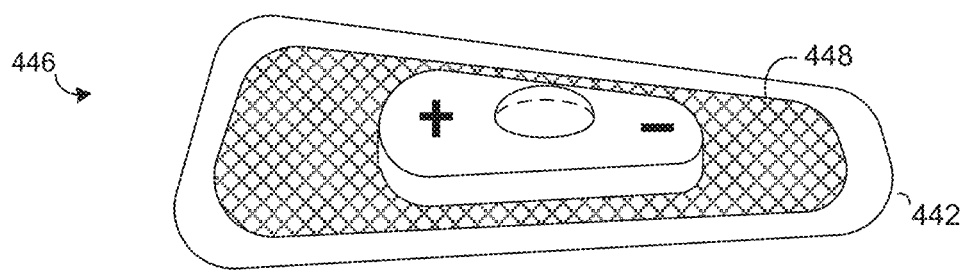
FIG. 4C is a plan view of an embodiment of a nonconductive housing that may be used with electrotherapy devices described herein.

FIG. 4C is a plan view of another embodiment of a nonconductive housing for an electrotherapy device 400 according to the present disclosure. In this aspect, the electrotherapy device includes a nonconductive housing 446 having a large flange 442 and a scaffold 448. The scaffold 448 in this aspect includes wire mesh, but other materials are suitable. Scaffold 448 is a supporting frame that can be bent manually into contoured surfaces or shapes to fit the electrotherapy device 400 to a user's body. The scaffold 448 can be shaped so that the housing 446 takes a desired shaped for fitting to the patient. For example, the desired contours can be configured so they are similar to the shape of the skin surface where the electrotherapy device 400 is attached, and the scaffold 448 can then retain such contours during use of the device. Such body-contour fitting scaffolds can help ensure the device fits tightly onto the user's skin surface, such that the interface between the skin and the contact surface of the electrotherapy device remains stable and consistent when a user is engaging in any number of activities, such as exercising or moving while sleeping, minimizing changes in current density across the contact surface. In addition, some embodiments of the housing 446 are dimensioned so as to allow the scaffold to be bent in such a way as to hold the device onto the user's body. For example, an electrotherapy device attached to a user's wrist can be wrapped around the wrist and held in place by the scaffold 448, similar to a wrist band. Other implementations are possible, such as bending the scaffold 448 to allow the electrotherapy device to wrap around an ankle, neck, or other portion of the user's body.

Figure 4D:
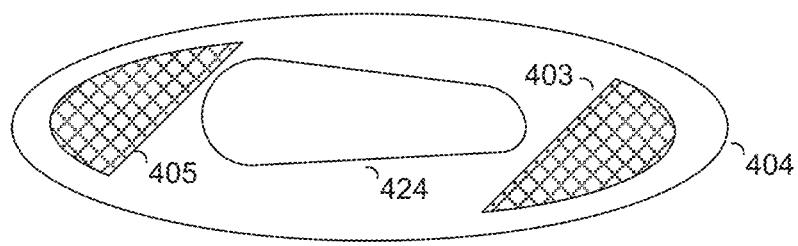
FIG. 4D is a plan view of an embodiment of a nonconductive top layer having a plurality of scaffolds.

Some embodiments of the scaffold are attached to the nonconductive top layer 404 of the electrotherapy device 400. In the embodiment illustrated in FIG. 4D, for example, scaffolds 403 and 405 are secured to the top of the nonconductive top layer 404. The scaffolds 403 and 405 can include wire mesh. In some implementations, scaffolds 403 and 405 are attached or disposed within other parts of the nonconductive top layer 404, or the housing 446. In addition to wire meshes, the scaffold can receive other shapes and structures, such as stripes and sheets. The scaffold can be made of conductive materials such as metals, or nonconductive materials such as plastics, for example.

Figure 4E:
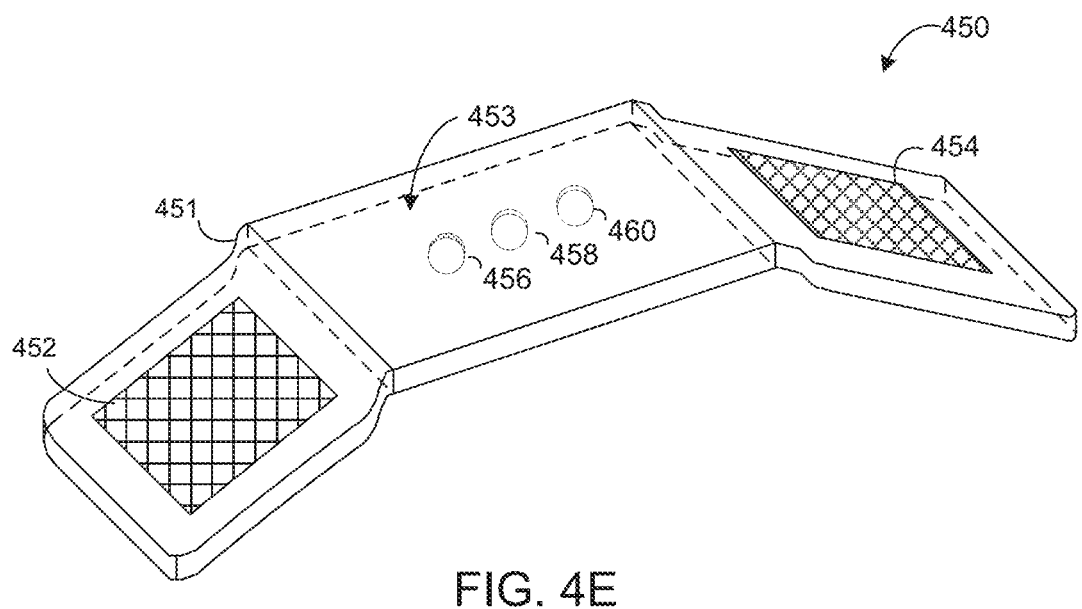
FIG. 4E is a plan view of an embodiment of an electrotherapy device having user-depressible input features.
Figure 4F:
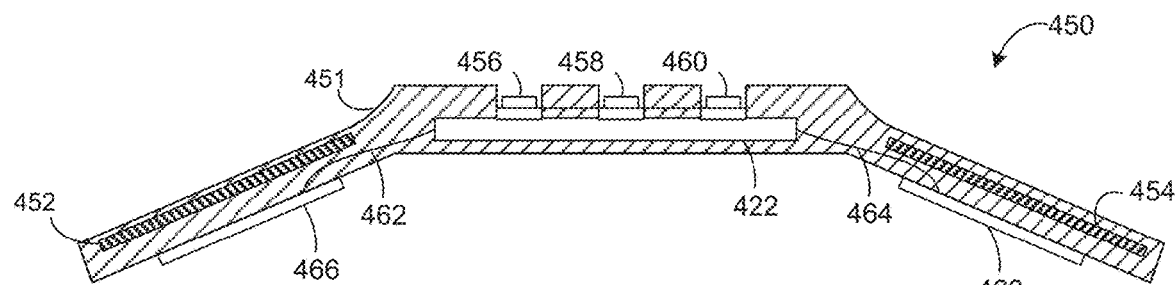
FIG. 4F is a cross-sectional view of the electrotherapy device of FIG. 4E.

FIGS. 4E and 4F depict plan and cross-sectional views of a non-invasive electrotherapy device 450 according to a further embodiment of the present disclosure. The electrotherapy device 450 includes a nonconductive housing 451 that is positionable on the patient's body and encloses an electronics layer 422 (shown in FIG. 4F), remote electrodes 466 and 468 (shown in FIG. 4F) electrically coupled to the electronics layer 422, and user-depressible buttons 456, 458, and 460. In this embodiment, scaffolds 452 and 454 are disposed within the nonconductive housing 451. As described above, the scaffolds 452 and 454 may include wire mesh or another suitable material.

The user-depressible buttons 456, 458, and 460 can actuate and control electronics included in the electronics layer 422. In this aspect, for example, user-depressible buttons 456, 458, and 460 are electrically coupled to switches in the electronics layer 422, which also connects electrically through lead wires 462 and 464 to remotes electrodes 466 and 468, respectively. Although three user-depressible buttons are shown in in FIGS. 4E and 4F, any number of user-depressible buttons can be implemented, and each can be configured for different functions. For example, buttons may be configured to adjust electrotherapy intensity, to power the device on or off, or to activate or deactivate communication circuitries, such as the wireless communication circuitry 106 and the wired communication circuitry 130 described with reference to FIG. 1D. Remote electrodes 466 and 468 are secured to the bottom surface of the housing 451 (e.g., by using snap connectors or by an adhesive). In some implementations, more than two electrodes are attached to the housing 451.

In FIG. 4E, three user-depressible buttons 456, 458, and 460 are disposed within the housing 451 such that their top surfaces are below a top surface 453 of the housing 451. The enclosure of these buttons within the housing can prevent unintentional actuation of electronics in the electronics layer 422, such as by pressing of the buttons 456, 458, and 460, during use of the electrotherapy device, for example during a vigorous exercise routine or while sleeping. While the electrotherapy device 450 includes user-depressible buttons 456, 458, and 460, embodiments of the electrotherapy devices according to the present disclosure can include other means for actuating electronics in the electronics layer 422, such as switches, dials, knobs, or other user input controls.

Figure 4G:
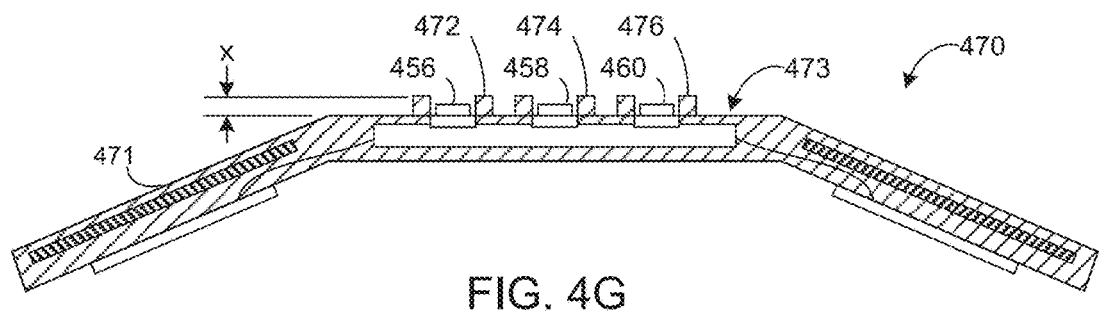
FIG. 4G is a cross-sectional view of an embodiment of an electrotherapy device having user-depressible buttons and button guards.

FIG. 4G is a cross-sectional view of an electrotherapy device 470 according to another implementation of the present disclosure. The electrotherapy device 470 includes a nonconductive housing 471 and a plurality of user-depressible buttons 456, 458, and 460. In this implementation, the user-depressible buttons 456, 458, and 460 are protected by a plurality of button guards 472a, 472b; 474a, 474b; and 476a, 476b, respectively. The button guards may be unitary extensions of the housing 471. In one example, the button guards may be co-molded with the housing. The button guards extend above a top surface 473 of the electrotherapy device 470 by a distance "x," as labeled in FIG. 4G. In certain implementations, this distance "x" is the same or about the same as a thickness of the button 456, where the thickness of the button 456 is measured from the top surface 473. In other aspects, the extension distance "x" is about 1.5 times or about 2 times the thickness of the button 456. It will be understood that each of the button guards 472a, 472b; 474a, 472b; and 476a, 476b can extend a different distance "x" above the top surface 473 of the electrotherapy device 470. By extending some distance above the top surface of the buttons being protected, the button guards can help shield the buttons 456, 458 and 460 from being pressed inadvertently during use of the electrotherapy device 470 (for example during lying down, sleeping, exercising, or other activities). In some implementations, the button guards are made of a material different from that used for the main body of the housing 471 to help provide tactile feedback so the user can locate the appropriate button to press.

Figure 4H:
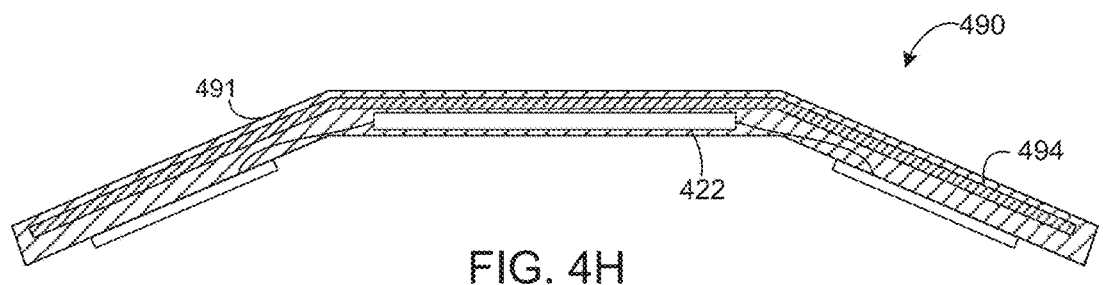
FIG. 4H is a cross-sectional view of yet another embodiment an electrotherapy device.

FIG. 4H is a cross-sectional view of an electrotherapy device 490 according to another aspect of the present disclosure. The electrotherapy device 490 includes a nonconductive housing 491 and a scaffold 494 that extends across the length of the nonconductive housing 491. In this embodiment, the electronics layer 422 is disposed within the nonconductive housing 491 and below the scaffold 494. In some implementations, the scaffold is placed below or around the electronics layer 422.

Figure 5:
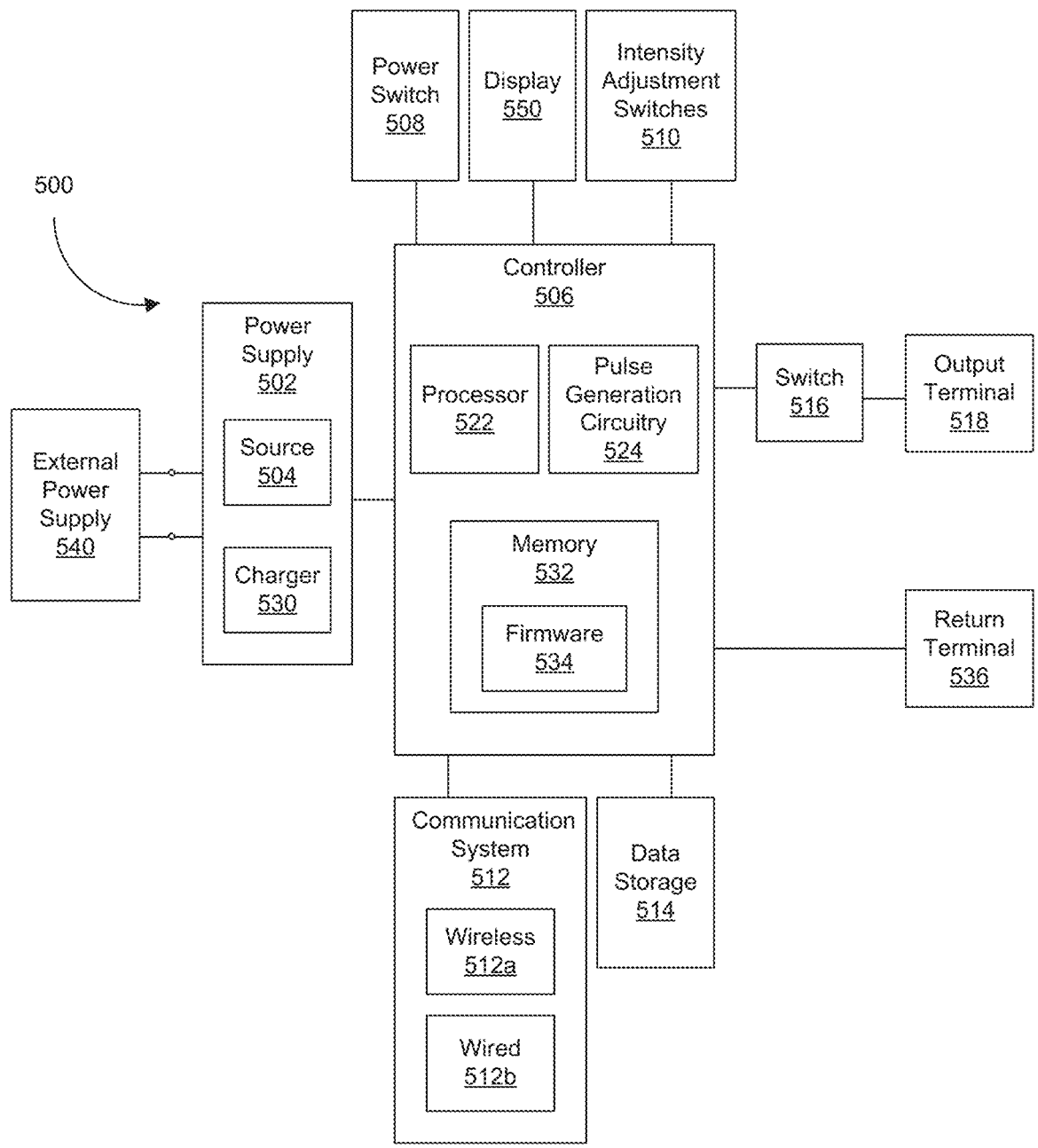
FIG. 5 is a block diagram of electronic components of an embodiment of an electrotherapy device.

FIG. 5 is a block diagram illustrating electronic components of an electrotherapy device 500 in accordance with the devices, systems, and methods described herein. The electrotherapy device 500 includes a power supply 502, a power source 504, a controller 506, a power switch 508, a display 550, amplitude or intensity adjustment switches 510, a communication system 512, a data storage device 514, a switch 516, an output terminal 518, and a return terminal 536. The electrotherapy device 500 may be similar to, or include the device 100 (FIG. 1A), the device 128 (FIG. 1C), the device 138 (FIG. 1D), the device 200 (FIG. 2), or the devices 400 (FIG. 4A), 450 (FIGS. 4E/4F), 470 (FIG. 4H), and 490 (FIG. 4H).

During normal operation, the power supply 502 receives power from the power source 504. The power source 504 may be a lithium-ion battery having a voltage of about 3.7 to 4.2 volts, although other battery types and voltages are used in some implementations. In some implementations, the power source 504 is flexible (e.g., a flexible battery). In some implementations, the power source 504 is fabricated using a layered painting technique as described by Singh et al. in "Paintable Battery," Scientific Reports, vol. 2, n. 481, 2012, incorporated by reference herein in its entirety. In this technique, a number of layers are deposited. The first layer acts as a positive current collector and includes purified single-wall carbon nanotubes with carbon black particles dispersed in N-methylpyrrolidone. The second layer acts as a cathode and includes lithium cobalt oxide, carbon, and ultrafine graphite (UFG) powder in a binder solution. The third layer acts as a polymer separator and includes Kynar Flex resin, PMMA, and silicon dioxide dispersed in a solvent mixture. The fourth layer acts as an anode and includes a mixture of lithium titanium oxide and UFG in a binder. The fifth layer acts as a negative current collector and includes conductive copper paint diluted with ethanol. Other layered painting techniques may be suitable for forming a flexible battery.

The power supply 502 may convert the energy supplied by the power source 504 to a desired voltage or current before supplying the power to other components of the electrotherapy device 500. For example, the power supply 502 may include a step-up converter to adjust or increase the voltage of power from the power source 504 to a desired voltage.

In this embodiment, the power supply 502 also includes a charger 530. The charger 530 receives power from an external power supply 540 and operates to recharge the power source 504. In some implementations, the external power supply 540 is a home or commercial power supply, such as those available through an electrical power outlet or computer port (e.g., USB). In some implementations, the external power supply 540 is a vehicle power supply, such as a supply accessible through a 12V receptacle. The charger 530 may monitor the charge level of the power source 504 (for example, with a thermistor to detect battery temperature). The charger 530 may also provide an indicator of the charge level of the power source 504. In some implementations, the charger 530 includes capacitive charging circuitry in electrical communication with the power source 504. The capacitive charging circuitry allows the device 500 to harness energy from a capacitive charging pad in proximity to the electrotherapy device 500 and capacitively coupled to the charger 530.

The controller 506 in this aspect is powered by the power supply 502 and controls the operation of the electrotherapy device 500. In particular, the controller 506 generates electrical signals that are provided to the output terminal 518. The controller 506 is electrically coupled to a power switch 508 and intensity adjustment switches 510. These switches may be similar to embodiments of the switches 222a, 222b, and 222c of FIG. 2 or the switches 416, 418, and 420 of FIG. 4A. The controller 506 monitors the state of the power switch 508. When the controller 506 detects that the state of the power switch 508 has changed, the controller 506 turns the electrotherapy device 500 on or off accordingly. The controller 506 also monitors the state of the intensity adjustment switches 510. When the controller 506 detects that the state of the intensity adjustment switches 510 has changed, the controller 506 increases or decreases the intensity of electrical signals provided to the output terminal 518 accordingly.

In certain embodiments, the intensity adjustment switches 510 are potentiometers. When one or more of the potentiometers is adjusted, the intensity of the electrical signal generated by pulse generation circuitry 524 is increased or decreased accordingly. The electrotherapy device 500 also includes a display 550 for communicating information about the status of the electrotherapy device 500 to the user. The display 550 may include one or more LEDs, one or more screens for text and graphic information, a touchpad interface for user command selection or input, or any combination of the foregoing.

When the electrotherapy device 500 is on, the controller 506 generates therapeutic electrical signals, and provides those signals through the output terminal 518 to a therapy site, such as therapy sites described below with reference to FIGS. 14A-15B. The switch 516 opens and closes the electrical coupling between the controller 506 and the output terminal 518. The output terminal 518 is electrically coupled to a conductive zone (e.g., either of the conductive zones 112a and 112b of FIG. 1A) that contacts the therapy site to deliver electrical signals to the user. After delivery to the therapy site, the electrical signal flows through the return terminal 536 back to the controller 506. The controller 506 includes a processor 522 (which may be similar to, include, or embody the computing circuitry 126 of FIG. 1C), which processes inputs for the therapy (including the stimulation parameters) and communicates with the pulse generation circuitry 524. Inputs for the therapy may be stored in memory 532, or may be derived from data received from another device (as described below with reference to communication system 512). The pulse generation circuitry 524 (which may be similar to or embody the pulse generation circuitry 108 of FIG. 1A or the pulse generation circuitry 224 of FIG. 2) receives an input from the processor 522 and generates a corresponding electrical waveform that is transferred to the output terminal 518 for delivery to a therapy site on a patient's tissue. As described above with reference to FIGS. 1-3, the output terminal 518 of the pulse generation circuitry 524 is in electrical contact with a first conductive zone that is applied to the patient's tissue. In some implementations, a current driver is included with the pulse generation circuitry 524 and is configured to drive current from the first conductive zone to a second conductive zone in electrical contact with the return terminal 536 when the first and second conductive zones are placed on a patient's tissue. The electrotherapy device 500 is configured to output multiple channels of electrotherapy, with each channel capable of providing a different electrotherapy waveform than the other channels.

In some implementations, the controller 506 includes timer circuitry (e.g., in communication with or internal to the processor 522) configured to track the amount of electrotherapy delivered by the pulse generation circuitry 524. The timer circuitry may track any one or more of time duration of delivered electrotherapy, a pulse count of delivered electrotherapy, and a number of delivered electrotherapy sessions, for example. The controller 506 may be configured to store the tracked amount information in the memory 532, the amount of power in the power source 504, and the computational power of controller 506. The tracked data can be analyzed to determine compliance with set standards.

The controller 506 includes the memory 532. Firmware 534 is stored in the memory 532. The firmware 534 includes software commands and algorithms that are executed by the controller 506 and defines logical operations performed by the controller 506. The software commands and algorithms in the firmware 534 may be used to operate the electrotherapy device 500 in a desired mode, such as a mode that provides transcutaneous electrical nerve stimulation therapy or muscle stimulation therapy.

The controller 506 may use the memory 532 for storing stimulation parameter or statistics regarding usage of the electrotherapy device 500. For example, information such as type of program, date, and frequency of treatments, and intensities applied may be recorded in the memory 532. Usage statistics may be uploadable from the memory 532 to a data storage device 514. The data storage device 514 is a device capable of storing data, such as a memory card or other known data storage device. In some implementations, the data storage device 514 is part of the memory 532. In certain implementations, current and historical operating parameters and physiological parameters (such as heart rate) are stored on the data storage device 514 and can be accessed by a user. The storage of usage data is described in additional detail below with reference to FIG. 7.

Usage statistics may also be uploadable to a remote data source via the communication system 512. The communication system 512 may include any or a combination of wireless communication circuitry 512a and wired communication circuitry 512b. Examples of wired communication circuitry 512b that may be included with the communication system 512 include a serial bus communication device (e.g., a Universal Serial Bus communication device), a local area networking communication device (e.g., an Ethernet communication device), and a wired modem. Examples of wireless communication circuitry 512a include a wireless area networking communication device (e.g., an 802.11x communication device), a wireless personal area networking (WPAN) device (e.g., a Bluetooth™ or Zigbee™ transceiver), or any other wireless communication device.

The communication system 512 can be used to receive data from another device (referred to herein as the "computing device"). The computing device may include a personal communication device, such as a cellular telephone device or an internet access device. For example, the computing device may be an iPhone device, a Blackberry device, an Android smartphone, or any other personal communication device. The computing device may include a media playing device, such as an MP3 player. In some implementations, the computing device is a personal computer, a server, or a mainframe, for example. In some implementations, the computing device is a portable computing device, such as a tablet device, net book, laptop, mobile telephone, smartphone, or any other such device. In some implementations, the computing device includes multiple computing devices, such as any of those described above. The computing device may include a computer running an operating system, such as but not limited to Windows (Microsoft), Linux, MacOS (Apple), Android (Google), iOS (Cisco Systems), Blackberry OS (Research In Motion), Symbian (Nokia), or Windows Phone (Microsoft) operating systems, for example.

The communication system 512 can be used to download different firmware 534 from the computing device to the electrotherapy device 500 to alter the operation of the controller 506, and operate the electrotherapy device in a desired mode, such as a mode that provides iontophoresis therapy. In some implementations, the wireless communication circuitry 512a decodes one or more electrotherapy programs from pulse generation control signals, or pulse generation data, received from a transmitter device, and stores the one or more decoded electrotherapy programs in a memory (such as the memory 532). In some implementations, the wired communication circuitry 512b can serve as a backup for the wireless communication circuitry 512a. For example, when wireless transmission is not allowed or deactivated, such as during a flight or a malfunction, pulse generation control signals can be transmitted through the wired communication circuitry 512b in a wired connection.

Although not illustrated in FIG. 5, either or both the communication system 512 or the controller 506 may be electrically coupled to a switch to deactivate one of the communication circuitries 512a and 512b when the other is activated. The communication system 512 and the controller 506 may also be coupled to separate power switches for each of the two communication circuitries. Embodiments of such switches are may be the same as or similar to the switches 222a, 222b, and 222c described with reference to FIG. 2 or the switches 416, 418, and 420 described with reference to FIG. 4A. In certain implementations, a firmware algorithm must be purchased before it can be downloaded by a user. In certain embodiments, a user must access a user interface of a web server or other similar interface before downloading a firmware algorithm.

In some implementations, the controller 506 operates the electrotherapy device 500 without relying on downloaded firmware. For example, the controller 506 may receive user input instructions via power switch 508, intensity adjustment switches 510, or from an external computing device through communication system 512, and adjust the electrical stimulation according to the user input in real time. The user may input information relating to, for example, power, intensity, and duration. The user may also select one or more modes of operation.

The communication system 512 may be used to transmit data to another device (such as the computing device discussed above). For example, the controller 506 may store a therapy log in the data storage device 514. The controller 506 can be used to upload the therapy log to an external device by transmitting a data log via the communication system 512. In some implementations, the wireless communication circuitry 512a includes a processor configured to encode, into a signal for wireless transmission to a computing device (not shown), at least one of a stored time duration of delivered electrotherapy, a stored pulse count of delivered electrotherapy, and a stored number of delivered electrotherapy sessions (e.g., as retrieved from the memory 532). Additional embodiments of the communication between a computing device and an electrotherapy device such as the device 500 are described below with reference to FIG. 12.

Figure 6A:
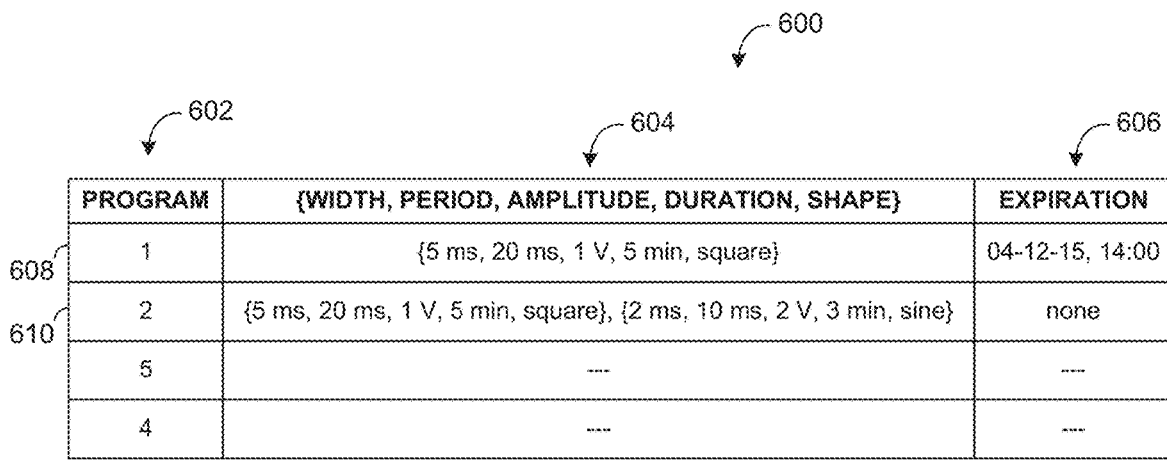
FIG. 6A illustrates a data structure for storing electrotherapy program data in a memory of an electrotherapy device according to one embodiment.

FIG. 6A illustrates a data structure 600 for storing electrotherapy program data in a memory. The data structure 600 may be stored in a memory of an electrotherapy device (such as the memory 532 of electrotherapy device 500), a computing device (such as the computing device 1200 discussed below with reference to FIG. 12), a remote memory (e.g., the database 1112 discussed below with reference to FIG. 11), or any combination of the foregoing. In this implementation, the data structure 600 includes two entries 608 and 610, each of which includes values for three fields: a program number field 602, a waveform details field 604, and an expiration field 606. The program number field 602 provides a simple way to index multiple electrotherapy programs stored in the data structure 600. The waveform details field 604 can store information used or required by the electrotherapy device in order to deliver the desired electrotherapy program. A waveform is the graphical depiction of a pulsed electrical current. Information stored in the waveform details field 604 may include pulse width, pulse period, pulse amplitude, program duration, pulse shape, inter-pulse interval, and any other information useful to specifying an electrotherapy waveform. The expiration field 606 can be used for electrotherapy programs which are only authorized for use in a finite time window or for a finite number of sessions; after the expiration time or number of uses, the corresponding electrotherapy program will no longer be accessible to the user. Not all electrotherapy programs need have an expiration value for the expiration field 606.

Figure 6B:
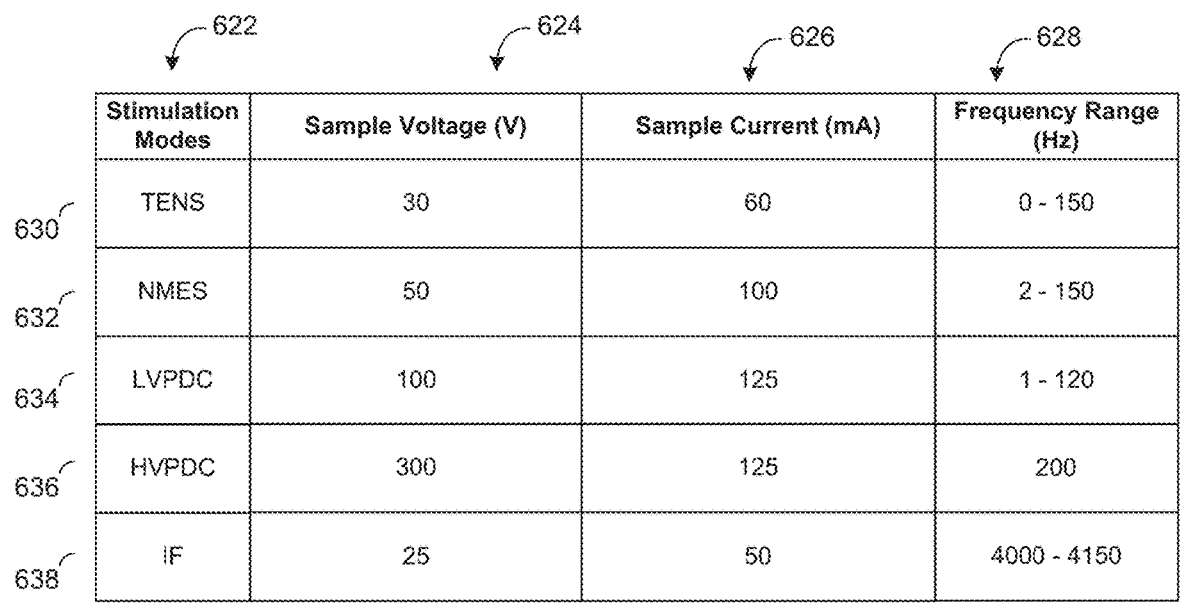
FIG. 6B lists sample electrotherapy stimulation modes embodiments of electrotherapy devices described herein can implement.

The devices, systems, and methods disclosed herein can be configured to apply electrotherapy using various stimulation modes and protocols. FIGS. 6B-6C illustrate example stimulation modes and protocols. FIG. 6B lists sample electrotherapy stimulation modes 622 for non-invasive electrotherapy, with corresponding sample voltages 624 in Volts (V), sample current amplitudes 626 in milliamps (mA), and the preferred stimulation frequency ranges 628 in Hz, or pulse per second (pps) (assumes that the load to the electrotherapy device is 500Ω). In one example, Transcutaneous Electrical Nerve Stimulation (TENS) mode 630 can provide pain relief at both relatively high frequencies in the order of about 130 Hz, and much lower frequencies in the order of 2-5 Hz, with a sample voltage at about 30V, and a sample current at about 60 mA. Stimulation frequencies generally fall within the range of 0 to about 150 Hz. Similarly, Neuromuscular Electrical Stimulation (NMES) mode 632 typically uses currents with greater energy than TENS to cause muscle contraction and the ability to rehabilitate muscle tissues.

In another example, Low Volt Pulsed DC current stimulation (LVPDC) mode 634, also called Low Volt Galvanic stimulation, uses voltage under about 180V to treat acute injuries associated with major tissue trauma with bleeding or swelling. Injured tissues are often surrounded by an excess of fluid, which prevents nutrient- and oxygen-rich blood from reaching them. In contrast to TENS, which applies alternating current, galvanic stimulators apply direct current, creating an electrical field over the treated area to change blood flow. Applying an electrotherapy device as described herein in LVPDC mode 634 can remove excess fluid and increases blood flow to the injured site to encourage rehabilitation. This stimulation mode uses two oppositely charged electrodes and is applied in two phases, first with a positive polarity over a time span (e.g., up to about 72 hours), then with a negative polarity. Similar to LVPDC mode 634, electrotherapy devices described herein operating in a High Volt Pulsed DC current stimulation (HVPDC) mode 636, also called High Volt Galvanic stimulation, use voltages to constrict vasculature and reduce edema (swelling). HVPDC mode 636 can be mainly used to treat high impedance body parts, like the foot, for which high voltage is requested. In some implementations, HVPDC mode 636 is applied with few pulses (e.g., only one pulse up to 500V). Nonetheless, two or more consecutive pulses (e.g., up to 300V) can be generated to help reduce the complexity and expense of electronic components.

Embodiments of electrotherapy devices operating in an Interferential Stimulation (IF) mode 638 use paired electrodes of two independent circuits carrying high-frequency and medium-frequency alternating currents. The superficial electrodes are aligned on the skin around the affected area. These frequencies interfere with the transmission of pain messages at the spinal cord. Because of the frequency, the IF wave encounters low impedance when crossing the skin to enter the underlying tissue. This tissue penetration can be adjusted to stimulate parasympathetic nerve fibers for increased blood flow. The high frequency helps penetrate the skin more deeply with less user discomfort than TENS. A further modification of IF is to pre-modulate (PreMod) the interferential waves, performing the interference between the high frequency and medium frequency alternating currents inside pulse generation circuitry, such as pulse generation circuitry 224 described with reference to FIG. 2A, and outputting the resulting attenuated waveform as the generated stimulation signal.

FIG. 6C illustrates example stimulation waveform shapes that can be stored in a data structure 600. Monophasic waveforms 648, biphasic waveforms 650, and a triphasic waveform 652 are presented, although other waveforms with more than three phases are also possible in some implementations. As shown by the graphical representations 646, monophasic waveforms 648 can contain a single pulse or more than one identical pulse, biphasic waveforms 650 can contain two non-identical pulses, while triphasic waveform 652 can contain three non-identical pulses. Each of the waveforms can be repeated over time according to a given stimulation frequency. Monophasic waveforms 648 can be direct current (DC) or interrupted DC. These can be used in applications such as iontophoresis, wound healing, edema reduction, tissue denervation, and innervated muscle contraction. Biphasic waveforms 650 are alternating current (AC), symmetrical or asymmetrical waveforms that can be used to suppress pain and to innervate muscle contraction. Triphasic waveform 652 contains three unbalanced pulses. This waveform can be used for edema reduction and pain suppression as well.

FIG. 7 illustrates a data structure 700 for storing usage data in a memory. This data structure may be stored in a memory of an electrotherapy device (such as the memory 532 of electrotherapy device 500), a computing device (such as the computing device 1200 discussed below with reference to FIG. 12), a remote memory (e.g., the database 1112 discussed below with reference to FIG. 11), or any combination of the foregoing. As shown, the data structure 700 includes four entries 708, 710, 712, and 714, each of which includes values for three fields: a start field 702, a stop field 704, and a program number field 706. The start field 702 records the time at which a user starts a particular electrotherapy program and the stop field 704 records the time at which the user stops the particular electrotherapy program. The program number field 706 provides a way to determine which of multiple electrotherapy programs are associated with the particular entry, and may use the same program number designations as in the program number field 602 in the memory structure 600 of FIG. 6.

Figure 8:
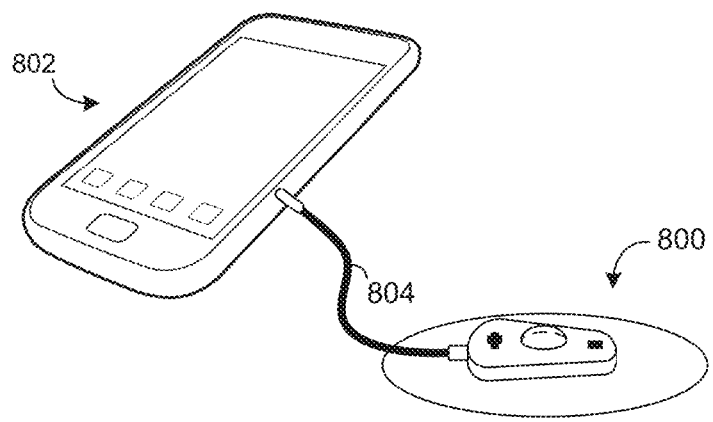
FIG. 8 is a perspective view of a computing device connected to an embodiment of electrotherapy device via an audio cable.
Figure 9:
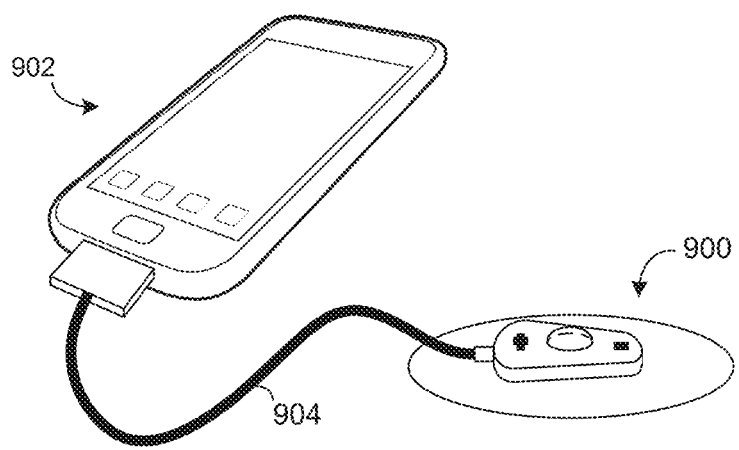
FIG. 9 is a perspective view of a computing device connected to another embodiment of an electrotherapy device via a serial communication cable.

The electrotherapy devices disclosed herein may be configured for wired communication with computing devices, in addition to or instead of wireless communication. FIG. 8 is a perspective view of a computing device 802 connected to an electrotherapy device 800 via an audio cable 804. Pulse generation control signals may be encoded into an audio signal and transmitted from the computing device 802 to the electrotherapy device 800 over the audio cable 804. These controls signals may be encoded at inaudible frequencies so that a user can continue to listen to music via a set of headphones connected to the audio jack of the device 802 at the same time that pulse generation control signals are sent from the audio jack to the electrotherapy device 800 via the audio cable 804. Other wired communication protocols may also be used. For example, FIG. 9 is a perspective view of a computing device 902 connected to an electrotherapy device 900 via a serial communication cable 904. The computing device 902 may encode pulse generation control signals using a serial communications protocol, and transmit those control signals to the electrotherapy device 900 over the serial communications cable 904.

Figure 10:
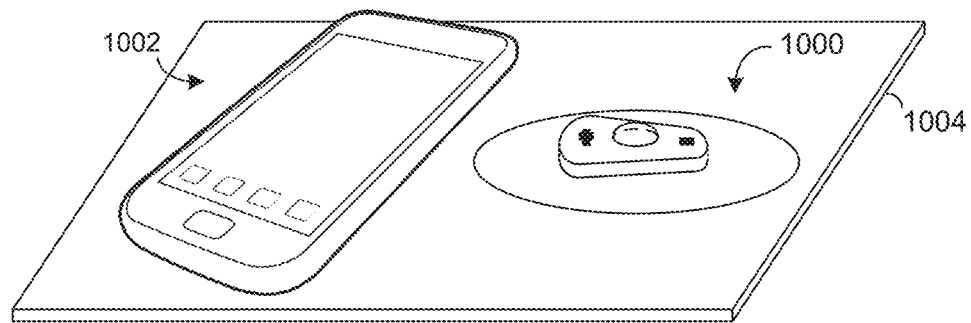
FIG. 10 is a perspective view of a computing device and yet another embodiment of an electrotherapy device positioned on a capacitive charging pad.

FIG. 10 is a perspective view of a computing device 1002 and an electrotherapy device 1000 positioned on a capacitive charging pad 1004. As described above with reference to FIG. 5, capacitive charging circuitry can be located within the computing device 1002 and the electrotherapy device 1000 to harness energy from the capacitive charging pad 1004 when the computing device 1002 and the electrotherapy device 1000 are in proximity to and in electrical communication with the capacitive charging pad 1004. In some implementations, the capacitive charging circuitry included in the electrotherapy device 1000 charges a flexible battery.

Figure 11:
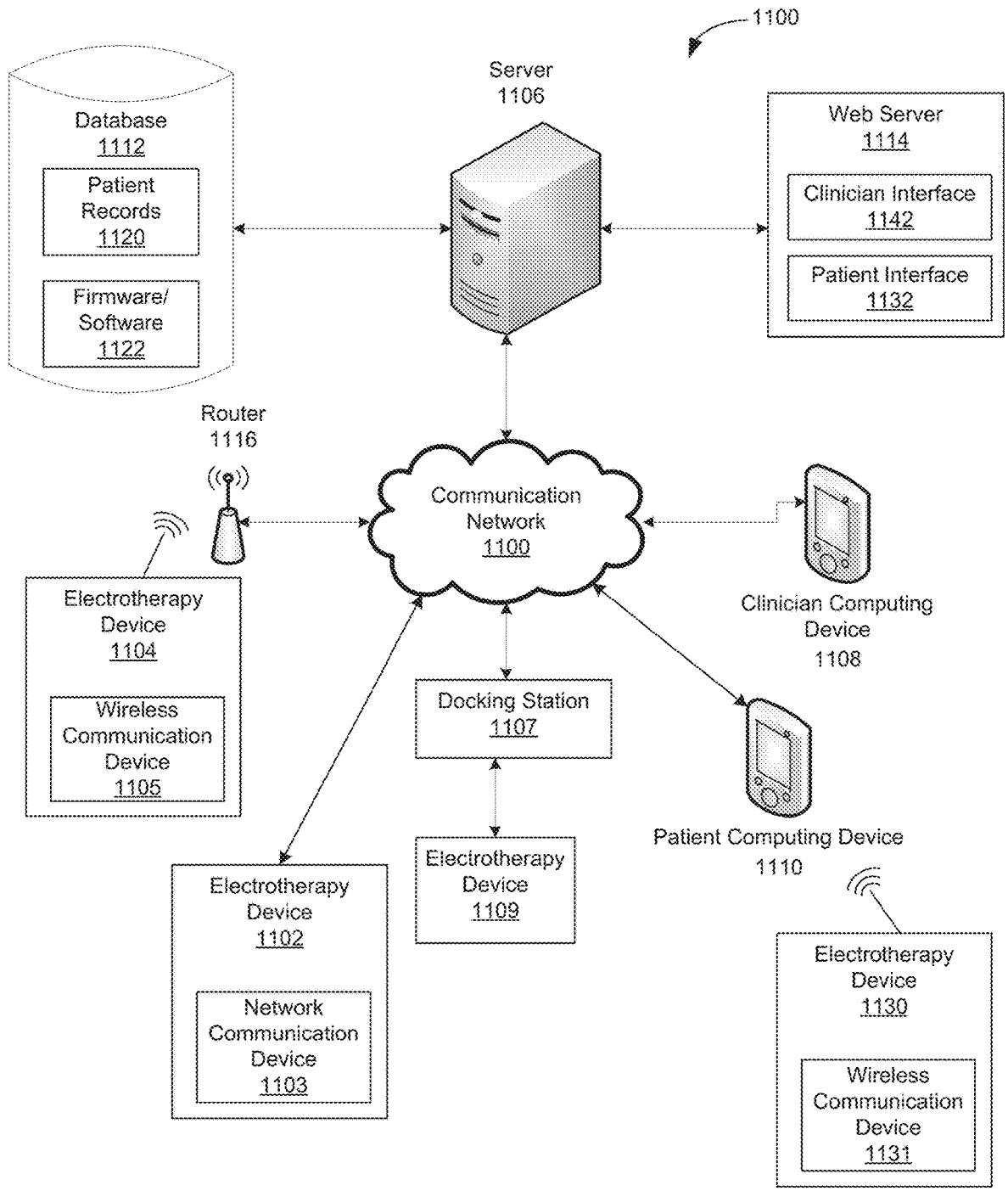
FIG. 11 is a block diagram of an embodiment of a system for communicating with an electrotherapy device across a communication network.
Figure 17:
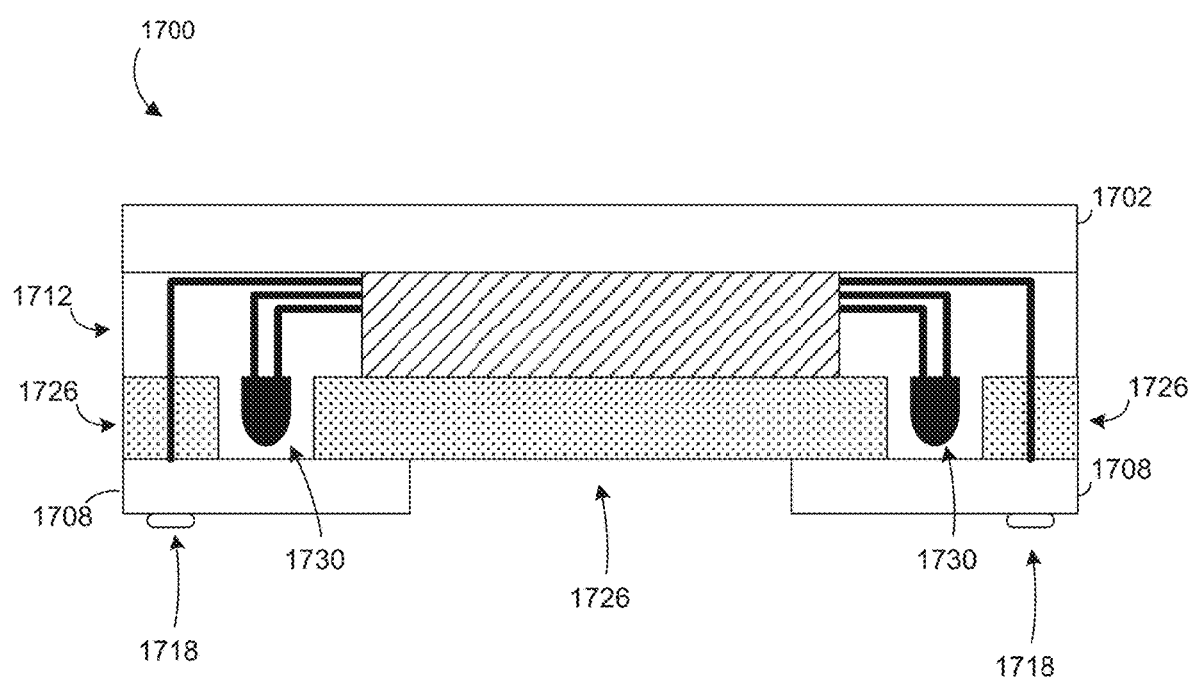
FIG. 17 is a cross-sectional view of an embodiment of an electrotherapy device including an integrated crosslinking energy source.

FIG. 11 is a block diagram of a system 1100 for communicating with an electrotherapy device across a communication network according to one embodiment of the present disclosure. In this implementation, the system 1100 includes a communication network 1150 configured to communicate with electrotherapy devices 1102, 1104, 1109, and 1130 using various communication connections. The electrotherapy devices 1102, 1104, 1109, and 1130 may include any combination of the components of the electrotherapy devices described herein, such as but not limited to components included in the electrotherapy devices 100, 200, 500, and 1700 (FIG. 17). In one example communication connection between an electrotherapy device of the present disclosure and the communication network 1150, the electrotherapy device 1109 is in data communication with a docking station 1107, which is in turn in data communication with the communication network 1150. In another example communication connection, the electrotherapy device 1104 includes a wireless communication device 1105 in communication with a wireless router 1116, which is in communication with the communication network 1150. Another example of a communication connection is illustrated with reference to the electrotherapy device 1102, which includes a wired network communication device 1103 that can communicate with communication network 1150. One implementation of this type of communication connection is described with reference to FIGS. 1A, 1B, and 1C (e.g., lead wire(s) 122). Still another example of a communication feature is depicted with reference to the electrotherapy device 1130, which includes a wireless communication device 1131 in communication with a patient computing device 1110, a clinician computing device 1108, or both. The patient communication device 1131 and the clinician computing device 1108 can be configured to communicate with the communication network 1150. In some implementations, the wireless communication circuitry included in the wireless communication devices described herein include a wireless personal area network (WPAN) transceiver, such as a Bluetooth™ transceiver or a ZigBee™ transceiver. The system 1100 also includes a server 1106 including, or in communication with a database 1112 and a Web server 1114. The system 1100 also includes a wireless router 1116, which, in one implementation described above, is in communication with an electrotherapy device of the system 1100.

As described above, the communication network 1150 can be a data communication network that communicates data signals between devices. In this particular example, the communication network 1150 is in data communication with the electrotherapy device 1109 (via the docking station 1107), the electrotherapy device 1102, the electrotherapy device 1104 (via the wireless router 1116), the server 1106, the electrotherapy device 1130 (via the clinician computing system 1108 and/or the patient computing system 1110), but other communication connections are possible. Examples of networks that may be included in the communication network 1150 include the Internet, one or more local area networks, one or more intranets, one or more near-field networks, one or more peer-to-peer networks, one or more ad hoc networks, and other communication networks.

In some implementations, the electrotherapy devices 1102, 1104, 1109, and 1130 store, in memory (not shown), data relating to therapy delivery or other operational characteristics of the respective devices. The communication network 1150 can be configured to communicate that stored data to another device for subsequent use, review, or processing. For example, data stored from one of the electrotherapy devices 1102, 1104, 1109, and 1130 may be transferred to a patient computing device such as device 1110 or to a clinician computing device, such as device 1108. Once the data has been transferred to the desired computing device, the data can be stored for review and analysis by the patient or the clinician, or it can be used to produce reports on usage, compliance, or other operational aspects of the electrotherapy devices 1102, 1104, 1109, and 1130.

The communication network 1150 can also be configured to communicate data from the electrotherapy devices 1102, 1104, 1109, and 1130 to the server 1106. In one example implementation, the server 1106 stores the data from an electrotherapy device as described herein in a patient record database 1120. In some implementations, the server 1106 includes or is in communication with a Web server 1114. The Web server 1114 can include a clinician interface 1142 and a patient interface 1132. In some implementations, additional interfaces are provided to third parties, such as an insurance company or a central clearinghouse for allowing clinicians to authorize the use of different electrotherapy programs for different patients. The Web server 1114 generates web pages that are communicated across the communication network 1150 using a standard communication protocol. An example of such a protocol is hypertext transfer protocol. The web page data is arranged in a standard form, such as hypertext markup language (HTML). The web page data is transferred across the communication network 1150 and received by the clinician computing device 1108, the patient computing device 1110, or both. Browsers operating on the respective computing devices read the web page data and display the web page to the user.

The clinician interface 1142 can also be configured to generate a web page intended for use by a clinician. The clinician interface 1142 can also allow the clinician to access the patient records database 1120 and generate reports or graphs to assist the clinician in analyzing data from the patient records database 1120. In addition, the clinician interface 1142 may provide technical or medical suggestions to the clinician. In some embodiments, the clinician interface 1142 also allows the clinician to request adjustments to an operational mode of an electrotherapy device (such as the electrotherapy devices 1102, 1104, 1109, and 1130) or to authorize additional electrotherapy programs for a particular user, as described below with reference to FIGS. 13A and 13B. The operational mode adjustments or authorizations are then communicated from the server 1106 to the appropriate electrotherapy device, and the electrotherapy device makes the appropriate adjustments.

The patient interface 1132 can be configured to generate a web page intended for use by a patient. In some implementations, the patient interface 1132 allows the patient to access the patient records database 1120 and generate reports or graphs that assist the patient in analyzing data from the patient records database 1120. The patient interface 1132 may provide instructions to assist the patient with uploading data from any of the electrotherapy devices 1102, 1104, 1109, and 1130 to the patient records database 1120. Other instructions or educational information may be provided by the patient interface 1132, if desired.

In some implementations, the database 1112 includes a firmware/software repository 1122. The firmware/software repository 1122 can include data instructions that define the logical operation of a controller for an electrotherapy device of the system 1100. The firmware/software repository 1122 is used in some implementations to store various versions of firmware. For example, when a new firmware version is created, the developer stores the new version of firmware in the firmware repository 1122. The firmware is then communicated to the electrotherapy devices 1102, 1104, 1109, and 1130 as appropriate. New firmware versions can be automatically distributed to the electrotherapy devices 1102, 1104, 1109, and 1130, or provided as an option to a patient or clinician through interfaces 1132 and 1142, respectively. In some embodiments, the patient interface 1132 requires that a patient agree to pay for an upgraded firmware version before the firmware is made available for installation on a device.

In another implementation, the firmware repository 1122 includes different firmware algorithms. Each firmware algorithm is specifically tailored to provide a specific therapy when executed by electrotherapy devices, such as electrotherapy devices 100 (FIG. 1A), 1102, and 1104, or is tailored to be used with a particular hardware configuration. Examples of therapies defined by separate firmware algorithms include migraine therapy, TENS, interferential therapy, edema therapy, muscle stimulation, nerve stimulation, iontophoresis therapy, and other therapies. A different firmware algorithm can also be specifically tailored for particular hardware configurations, such as for particular numbers or configurations of conductive zones, for particular communication devices, for different docking stations, or to accommodate other differences in hardware configuration.

For example, a patient may first obtain an electrotherapy device, such as the electrotherapy device 1130. The electrotherapy device 1130 includes a first firmware type that defines an algorithm appropriate for migraine therapy. Later, the patient desires to upgrade the device to cause the device to operate as an iontophoresis therapy device. To do so, the patient uses the patient computing system 1110 to access the patient interface 1132. The patient selects a new firmware algorithm that is designed for iontophoresis therapy. The patient downloads (in some cases after purchasing) the firmware associated with the iontophoresis therapy and loads the firmware onto the electrotherapy device 1130. If necessary or desired, appropriate accessories (such as hydrogel patches or sprays) can be purchased through the patient interface 1132 and delivered to the patient. The new firmware algorithm is then executed, causing the electrotherapy device to provide the desired electrical stimulation therapy. In one aspect, the electrotherapy device is configured to provide iontophoresis therapy. In this way, some implementations of the electrotherapy devices described herein are customizable to provide multiple different therapies. In some implementations, firmware is specially tailored for providing a therapy to a particular part of the body. As a result, different firmware algorithms are available for the treatment of different body parts and conditions associated with those body parts. Such firmware algorithms can be obtained by downloading, as described above. Examples of such implementations are described below with reference to FIGS. 13A and 13B.

Figure 12:
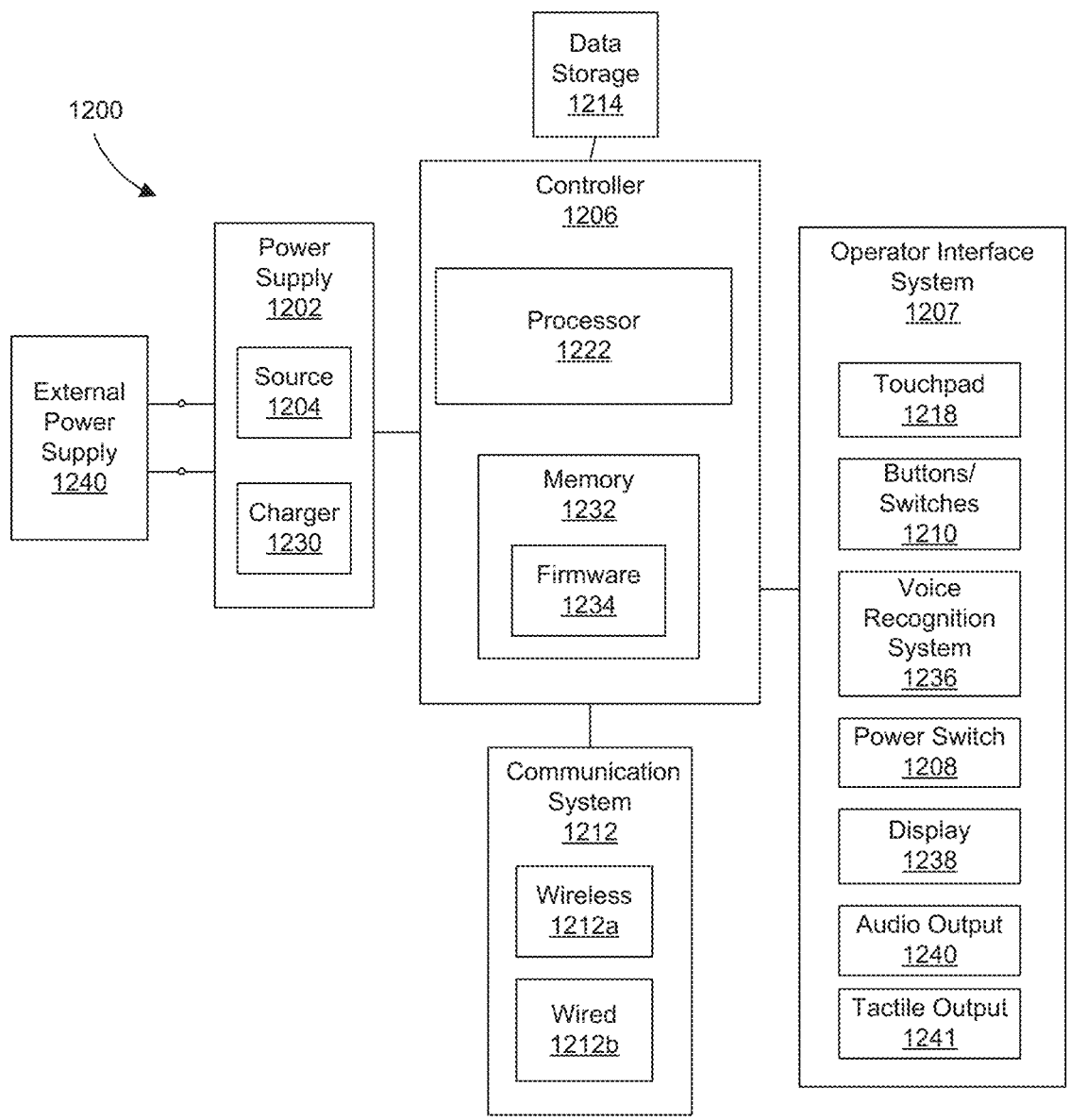
FIG. 12 is a block diagram of electronic components of an embodiment of a computing device.

FIG. 12 is a block diagram of electronic components of a computing device 1200 according to one embodiment of the present disclosure. The computing device 1200 can be the same as or similar to the patient computing device 1110 or the clinician computing device 1108 described with reference to FIG. 11, and can be configured to communicate with an electrotherapy device (such as any of the electrotherapy devices 1102, 1104, 1109, and 1130 described with reference to FIG. 11). The components of the computing device 1200 may be configured as processor-executable code in a general or special purpose processing device (e.g., a programmable microprocessor), logic circuits, analog circuits, or any combination of hardware, and software configured to provide therapeutic stimulation and perform the stimulation interference avoidance techniques described herein. The following components of the computing device 1200 are described separately, but the functionality of any one or more of any of the components described herein may be implemented together in one or more control circuits.

In one embodiment, the computing device 1200 communicates with the electrotherapy device 500 to specify an electrotherapy program to be provided to the user. The computing device 1200 uses stored programs and user inputs to determine the electrotherapy waveform provided to the user by specifying certain waveform parameters to the electrotherapy device 500 such as amplitude, pulse duration, pulse frequency, and pulse shape. The computing device 1200 can manage more than one output channel in a multi-channel electrotherapy device. Multiple channels may operate simultaneously, alternately, or in any other time-based relation. The electrotherapy program delivered by each channel may be customized and adjusted by an operator, who may be a clinician or the user him/herself. For example, an operator may control the intensity and/or energy output on each electrotherapy channel.

The computing device 1200 includes an operator interface system 1207 that allows an operator to select electrotherapy programs, set desired options, and control the waveforms applied to the user. The computing device 1200 includes one or more processors (e.g., microprocessors) that communicate with and control the operation of the electrotherapy device 500, providing an interface between the electrotherapy device 500 and an operator managing the therapy applied to the user. In some implementations, the computing device 1200 transmits information to and receives information from the electrotherapy device 500 using the wireless communication system 1212a through a wireless communication protocol. The computing device 1200 may also access a remote data source (such as the database 1112 of FIG. 11).

In some implementations, the computing device 1200 is housed in a handheld unit with an outer casing that encloses an electronics board on which are mounted the electronic components described below. The outer case can be formed of or include plastic or any other suitable material. The computing device 1200 may be waterproof or water-resistant (e.g., sweat or water are not permitted to penetrate the casing), and in some cases is operable with one adult hand. In some implementations, the computing device 1200 is a personal communication device, such as a cellular telephone device or an internet access device. For example, the computing device may be an iPhone device, a Blackberry device, an Android smart phone, an iPad, or any other personal communication device. The computing device 1200 may include a media playing device, such as an MP3 player. The electrotherapy control features and functions of the computing device 1200 may be implemented via software or firmware, as described above with reference to FIG. 11.

FIG. 12 depicts a number of systems that can be included in the computing device 1200. The operator interface system 1207 allows an operator to adjust the electrotherapy waveform delivered to a user by the electrotherapy device 500, view current operating parameters, view historical user data (such as performance and use statistics), view current physiological parameters (such as chemical or electrical muscle feedback signals), and adjust the capabilities of the electrotherapy device 500 (e.g., by downloading additional programs to the computing device 1200 from a remote data source).

The operator interface system 1207 may include any number of outputs, including an audio output 1240 (e.g., a speaker or buzzer), a visual display 1238 (e.g., an LCD screen or one or more LEDs), and a tactile output 1241 (e.g., a vibrating element). The operator interface system 1207 is not limited to these output features, however. For example, the operator interface system 1207 may include any number of user inputs, such as but not limited to a power switch 1208, other switches/buttons 1210, a touchpad 1218, including non-tactile inputs such as microphones (included in a voice recognition system 1236, in one example), and cameras. In certain implementations, the operator interface system 1207 includes a "help" button that sends alarm signals to a personal emergency response system.

The computing device 1200 may also include controller 1206 having a processor 1222 and a memory 1232. The processor 1222 may be employed to determine whether an electrotherapy device (such as the electrotherapy device 500 of FIG. 5) has been detected and then whether an activation or launch command has been received through the operator interface system 1207. The memory 1232 may serve as data storage for receiving commands or further include firmware 1234 configured to execute the processes disclosed herein. The interaction of the processor 1222 with other components of the computing device 1200 is discussed below with respect to FIGS. 13A and 13B.

The computing device 1200 may include a power supply 1202, which may include any suitable energy source 1204 for powering the components of the computing device 1200. In certain implementations, the power supply 1202 includes one or more of a battery (which may be a rechargeable battery), an AC power supply, a solar cell, a thermal cell, or a kinetic cell capable of converting motion energy to electrical energy for powering the computing device 1200. The computing device 1200 may contain multiple power supplies, any of which may be any of the power supplies described herein.

The computing device 1200 may also include power supply monitoring circuitry (not shown). Such circuitry may monitor the power supply 1202 of the computing device 1200 and/or the power supply 502 of the electrotherapy device 500 (FIG. 5). When the computing device 1200 and/or the electrotherapy device 500 does not have enough power left to complete a desired treatment or therapy, an indication is presented (e.g., on a visual display or via an audible output included with the operator interface system 1207) that indicates insufficient power is available. In this situation, an operator may be prohibited from accessing certain functions of the electrotherapy device 500 (e.g., beginning a new round of stimulation treatment).

The computing device 1200 (as well as any device or system component described herein) can include a data storage 1214 for storing basic operating parameters (e.g., pre-stored sounds, volume, display parameters, time, and date) and/or supporting the systems described herein. In certain implementations, usage statistics are uploadable from this data storage 1214 to a remote data source when the computing device 1200 is in communication with the remote data source. The data storage 1214 can also store one or more electrotherapy programs. In one non-limiting example, the data storage 1214 is capable of storing at least 15 different electrotherapy programs.

The computing device 1200 generates signals that are communicated to the electrotherapy device 500, instructing the electrotherapy device 500 to provide electrotherapy according to a prescribed electrotherapy program. As used herein, an electrotherapy program refers to one or more electrotherapy waveforms (e.g., a succession of electrical pulses). For example, a program may be provided to improve a particular muscle condition, such as "endurance," "force," or "active recovery." A program may be described by any one or more of the following parameters: pulse width, pulse duration, frequency, changes in frequency, treatment duration, warm up phase parameters, work phase parameters, and recovery phase parameters.

The computing device 1200 may include a communication system 1212, having a wireless communication system 1212*a* configured for wireless communication with the electrotherapy device 500. This wireless communication may be an RF-based protocol, and may use a proprietary or public communications protocol. In some implementations, a wireless area network communication protocol such as 802.11x is employed. In some implementations, the wireless protocol is a Bluetooth™ or a ZigBee™ protocol. In some applications, the communication system 1212 communicates with the electrotherapy device 500 when they are spaced apart (for example, about 2 meters apart) although the computing device 1200 and the electrotherapy device 500 may be configured for communicating when separated by more or less than this distance.

The communication system 1212 may be separated into two or more different systems: one system for communication between the computing device 1200 and the electrotherapy device 500 as described above, and a separate system for communication between the computing device 1200 and a remote data source (such as the database 1112 of FIG. 11), each driven and controlled by different control circuits. The communication system 1212 may include a wired communication system 1212*b*, in addition to or instead of the wireless communication system 1212*a*. The wired communication system 1212*b* may include any number of wired communication devices, such as a USB port for connecting a USB cable between the computing device 1200 and the electrotherapy device 500 or another computing device, an audio jack for connecting an audio cable between the computing device 1200 (over which data may be transmitted as discussed above with reference to FIG. 9). In some implementations that include a computer communicably coupled between the computing device 1200 and a remote data source, the communication system 1212 enables the computing device 1200 to communicate with the remote data source via the computer. In some implementations, the communication system 1212 communicates directly with the remote data source without the need for an intermediate computer (e.g., via a wireless Internet or device-to-device connection such as a Bluetooth™ connection).

The wireless communication system 1212a can maintain wireless communication with one or more electrotherapy devices such as the electrotherapy device 500 (but may be wired in some implementations). When the computing device 1200 loses communication with any one or more electrotherapy devices (e.g., because of an out-of-range condition, power loss, operating error, or break in communication arising from interference with another device), all active electrotherapy devices (e.g., every device currently delivering or preparing to deliver an electrotherapy treatment) may stop, and a pause mode may begin. A display may present an operator with an opportunity to attempt to re-initialize the communication between the electrotherapy device and the computing device 1200. When communication is successfully re-established, an operator may instruct the computing device 1200 to re-commence any paused programs or preparations. An operator may also abort the treatment at the time of loss of communication and/or when communication is successfully re-established.

Figure 13A:
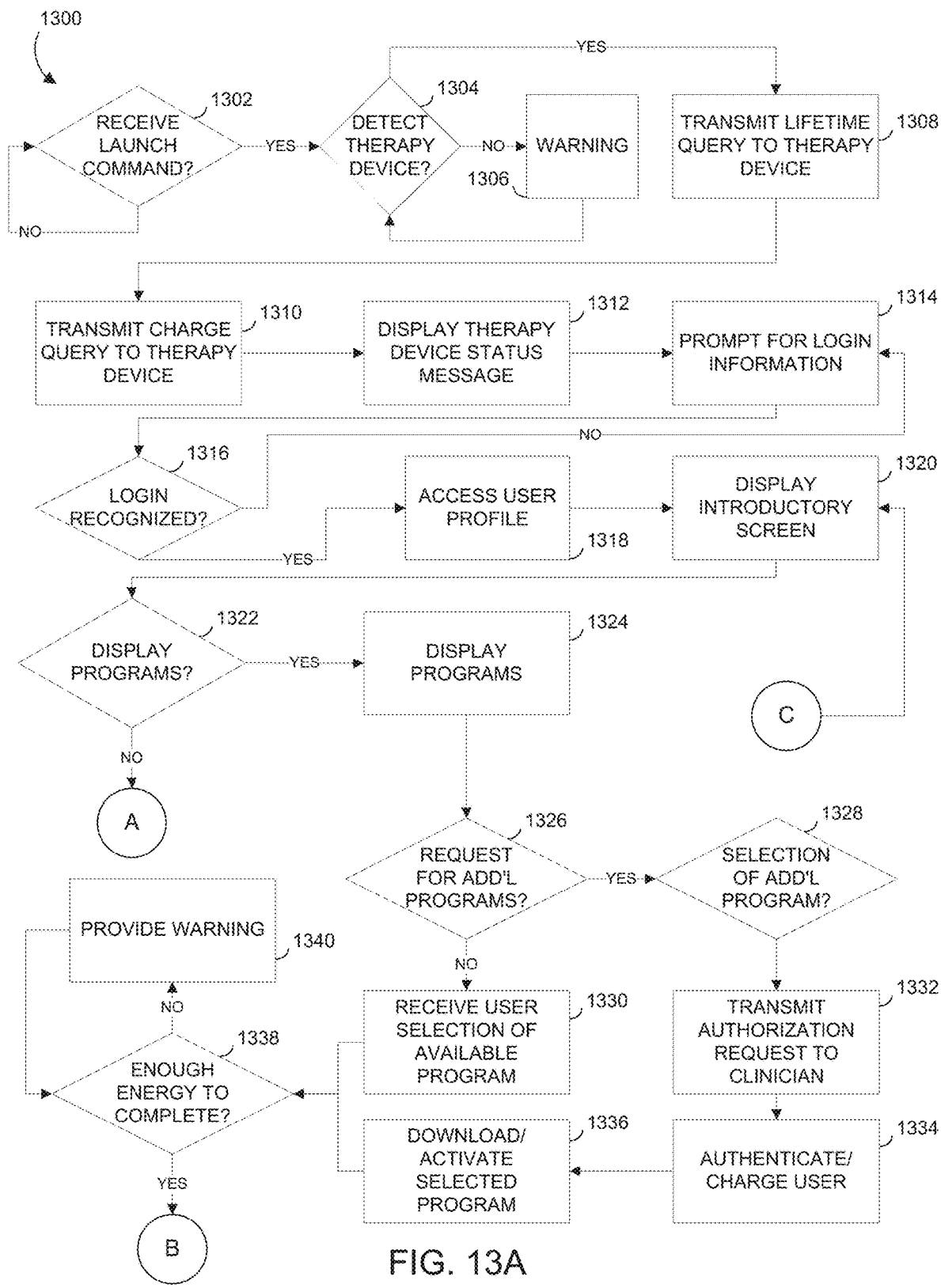
FIGS. 13A and 13B are a flow diagram illustrating a method of operating a computing device configured to communicate with an electrotherapy device according to an embodiment of the present disclosure.
Figure 13B:
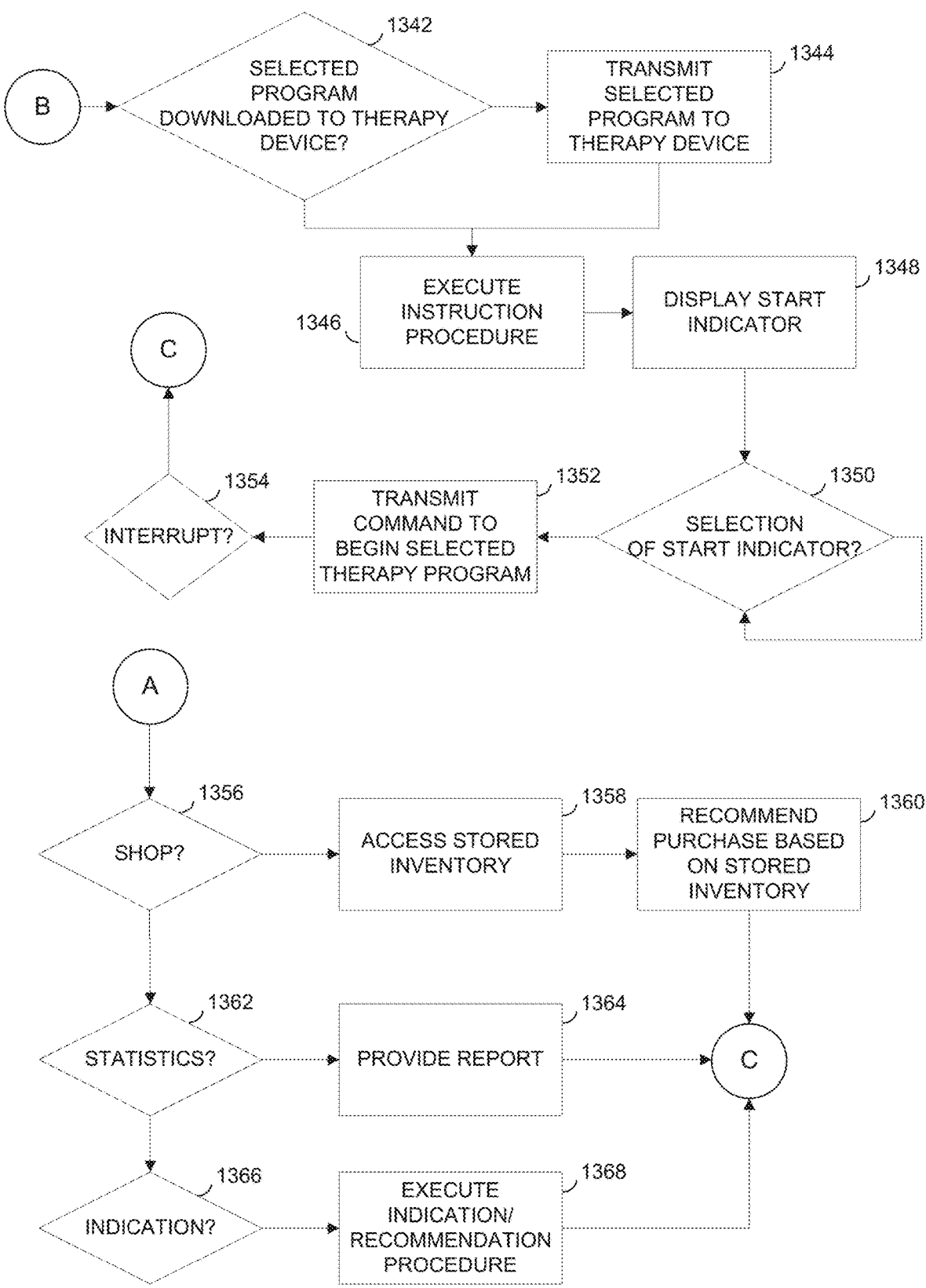

FIGS. 13A and 13B are a flow diagram illustrating a method 1300 of operating a computing device configured to communicate with an electrotherapy device according to one embodiment of the present disclosure. For ease of illustration, various steps of the method 1300 are described as performed by the processor 1222 of the computing device 1200 (FIG. 12) in communication with the electrotherapy device 500 (FIG. 5), but these steps may apply to any combination of computing devices and electrotherapy devices described herein. For example, in some implementations, the computing device 1200 is a personal communications device (such as a cellular telephone or a handheld internet access device).

The method 1300 begins at step 1302, in which the processor 1222 determines whether a launch command has been received. A launch command could be received from any of a number of sources. For example, a launch command can be received from a user input on the touchpad 1218 of the computing device 1200; a user activation button or switch (such as the buttons/switches 1210) on the computing device 1200; a user voice command received by the voice recognition system 1236 of the computing device 1200; or any other mechanism by which a user command may be received by the computing device 1200.

The method 1300 then moves to step 1304, in which the processor 1222 determines whether an electrotherapy device (such as but not limited to the electrotherapy device 500 of FIG. 5) has been detected. In implementations in which the computing device 1200 is connected to the electrotherapy device 500 via a wired connection, the step 1304 may be executed by determining whether a satisfactory wired connection has been established between the computing device 1200 and the electrotherapy device 500 (e.g., whether a connection having an expected impedance has been established). In implementations in which the computing device 1200 wirelessly connects with the electrotherapy device 500, the step 1304 may be executed by querying all of the wireless devices in proximity to the computing device 1200 and determining whether any of them are identified as electrotherapy devices with which the computing device 1200 can communicate. If the processor 1222 does not detect an electrotherapy device 500 at step 1304, the computing device 1200 may issue a warning to the user (e.g., via the display 1238 or the audio output 1240) at step 1306 indicating that no electrotherapy device has been found with which the computing device 1200 can communicate.

If the processor 1222 does detect the electrotherapy device 500 at step 1304, the method proceeds to step 1308 in which the processor 1222 transmits a lifetime query to the detected electrotherapy device 500. The lifetime query requests information regarding the allowed remaining use of the electrotherapy device 500. A lifetime query may be appropriate in implementations in which the electrotherapy device 500 is a limited use device. For example, the electrotherapy device 500 may be rated for a maximum of five hours of use before the reliability of one of the components of the electrotherapy device 500 decreases below an acceptable threshold. In response to the lifetime query, the electrotherapy device 500 may transmit a status message to the computing device 1200, which may indicate that the electrotherapy device 500 has expired or is still available for use. The electrotherapy device 500 may also indicate to the computing device 1200 how many uses remain, or the duration of remaining use.

Moving next to step 1310, the processor 1222 transmits a charge query to the electrotherapy device 500. The charge query requests information about the power available at the electrotherapy device 500 for delivering electrotherapy. In some implementations, the electrotherapy device 500 responds to the charge query by indicating the percentage charge remaining on a battery included in the electrotherapy device 500. In some implementations, the electrotherapy device 500 responds to the charge query by indicating the duration of electrotherapy that can be delivered with the available power, which may be based on a default electrotherapy program or other default power usage.

The method 1300 next moves to step 1312, in which the processor 1222 displays an electrotherapy device status message on a display, such as the display 1238 included with the computing device 1200. The electrotherapy device status message may reflect the information received at the computing device 1200 in response to the lifetime query, the charge query, both queries, or any other query or information about the electrotherapy device 500 known to the computing device 1200.

The method 1300 then moves to step 1314, in which the processor 1222 prompts the user of the computing device 1200 for login information. The login information may include a user name, a password, biometric identification information, or any other information suitable for identifying a user to the computing device 1200. User inputs to the computing device 1200 (including login information, option selection, and other inputs) may be received via the touchpad 1218, the buttons/switches 1210, the voice recognition system 1236, or any other input interface of the computing device 1200. The processor 1222 may compare the login information received in response to the prompt of step 1314 to stored validation information. The stored validation information may be stored locally to the computing device 1200 or may be stored remotely from the computing device 1200 (e.g., at an Internet-accessible remote server).

If the processor 1222 recognizes the login information at step 1316, the method 1300 proceeds to step 1318, in which the processor 1222 accesses a profile associated with the user from a memory. The memory from which the user profile is accessed may be local or remote. A user profile may store any of a number of different types of information about a user, such as but not limited to the user's goals, medical indications, purchase history, electrotherapy use history, contact information, clinician information, and device capabilities.

At step 1320, the processor 1222 next displays an introductory screen to the user via the display 1238. The introductory screen includes a number of options from which the user can select. These options can include a PROGRAMS option, a SHOP option, a STATISTICS option, and an INDICATION option. If the processor 1222 determines at step 1322 that the user has selected the PROGRAMS option, the method 1300 proceeds to step 1324 and displays a list of the electrotherapy programs that are available for delivery by the electrotherapy device 500. A program may be "available" if the program is stored locally to the computing device 1200, stored locally to the electrotherapy device 500, available to the user without additional payment or other authorization, or any combination of the foregoing. The available programs in the displayed list may be user-selectable. The display that includes the available programs list may also include a user selectable option to request additional programs.

If the processor 1222 determines at step 1326 that the user has selected the option to request additional programs, additional programs for the user available for selection are displayed for the user. This list of additional programs may be retrieved from a local memory or from a remote memory (not shown). These additional programs may be programs that are not stored locally to the computing device 1200, programs that are not stored locally to the electrotherapy device 500, programs that are available to the user upon additional payment or other authorization, or any combination of the foregoing.

If the processor 1222 determines that the user has selected one of the additional programs at step 1328, the method 1300 moves to step 1332 in which the processor 1222 transmits an authorization request to a clinician. This authorization request may take the form of an email directly to the clinician or an electronic query sent to a centralized authorization clearinghouse accessible by the clinician, for example. If the clinician authorizes the request (e.g., by sending a reply e-mail with an authorization code, or logging in to the centralized authorization clearinghouse and indication authorization through an Internet interface), the method 1300 proceeds to step 1334 in which the user is charged for access to the selected program. Once the user has been charged, the method 1300 proceeds to step 1336 in which the selected program is added to the available programs list for that user. In some implementations, access to an additional program does not require clinician authorization, additional payment, or both, and the processor 1222 does not perform the corresponding steps.

If the processor 1222 determines at step 1326 that the user has not requested a list of additional programs, the method 1300 proceeds to step 1330 and waits to receive a user selection of a program in the available programs list. Once a program has been selected, the method 1300 moves to step 1338 in which the processor 1222 determines whether the electrotherapy device 500 has enough available energy to complete the selected program. The processor 1222 uses the information provided by the electrotherapy device in response to the charge query (transmitted at step 1310) in order to determine whether the electrotherapy device 500 has sufficient energy. The processor 1222 may calculate the energy required (e.g., by performing a numerical integration of the product of the expected current and voltage over the course of the electrotherapy program) or may receive an estimate or range of estimates of the energy required by the electrotherapy program when information about the electrotherapy program is first stored in the computing device 1200. If the processor 1222 determines that the electrotherapy device 500 does not have sufficient energy to deliver the selected electrotherapy program, the processor 1222 provides a warning to the user at step 1340.

If the processor 1222 determines that the electrotherapy device 500 does have enough charge to complete the selected program, the method 1300 proceeds to step 1342 to determine whether the selected program has previously been downloaded to the electrotherapy device 500. If the selected program has not been previously downloaded, the method 1300 proceeds to step 1344 in which the processor 1222 transmits pulse generation control signals representative of the electrotherapy program to the wireless communication circuitry of the electrotherapy device 500. In some implementations, the electrotherapy programs are not stored locally to the electrotherapy device 500; in such implementations, steps 1342 and 1344 may not be performed. Once a selected program is available to the electrotherapy device 500, the method 1300 proceeds to step 1346 in which the processor 1222 executes an instruction procedure. The instruction procedure provides information to a user (e.g., via the display 1238) on how to properly configure the electrotherapy device 500 on their tissue and begin the delivery of electrotherapy. In some implementations, the instruction procedure is communicated to the computing device 1200 as a web page via the patient interface 1132 of the Web server 1114 of FIG. 11. The instruction procedure may include visual instructions, audible instructions, or a combination of both. The instruction procedure may be interactive, requiring the user to proceed in stages and confirm that the electrotherapy device 500 has been properly positioned before electrotherapy can begin.

The method next moves to step 1348, in which the processor 1222 displays a START indicator on a display 1238 of the computing device 1200. The START indicator may be user-selectable. If the processor 1222 determines at step 1350 that the user has selected the START indicator, the method 1300 proceeds to step 1352 and the processor 1222 transmits a command to the electrotherapy device 500 to begin the selected electrotherapy program. In implementations in which the electrotherapy program is not stored locally to the electrotherapy device 500, the processor 1222 may continue to transmit signals to the electrotherapy device 500 that instruct the electrotherapy device on the waveform to provide. In implementations in which the electrotherapy program is stored locally to the electrotherapy device 500, the processor 1222 may proceed to step 1354 and wait for an interrupt signal from the user. Until an interrupt signal is received, the electrotherapy device 500 will continue to deliver the electrotherapy program. If no interrupt signal is received, the selected electrotherapy program will proceed until it ends. If the processor 1222 receives an interrupt signal from the user (e.g., by the user pressing a stop button on the computing device 1200), the method 1300 may end. In one aspect, the method returns to step 1320 and displays the introductory screen if an interrupt signal is received.

As discussed above, the introductory screen displayed at step 1320 may include a number of user-selectable options. If the user does not select the PROGRAMS option at step 1322, the method 1300 proceeds to step 1356 in which the processor 1222 determines whether the user has selected the SHOP option. If the user has selected the SHOP option, the method 1300 proceeds to step 1358 in which the processor 1222 accesses an inventory from a local or remote memory. The inventory reflects the electrotherapy devices and accessories that have been previously purchased or obtained by the user (for example, gels and disposable electrodes). By accessing the stored inventory in response to a SHOP request, the processor 1222 may determine which devices and accessories the user may be in need of or wish to buy, and recommend those devices and accessories to the user at step 1360. In some implementations, the processor 1222 may recommend a set of devices and accessories by listing those devices and accessories first (or otherwise highlighting those devices and accessories) in a list of purchasable devices and accessories displayed to the user. After the user completes any desired purchases, the method 1300 may return to step 1320 where the introductory screen is displayed.

If the user does not select the SHOP option at step 1356, the flow diagram 1300 proceeds to step 1362 and the processor 1222 determines whether the user has selected the STATISTICS option. If the user has selected the STATISTICS option, the flow diagram 1300 proceeds to step 1364 in which the processor provides a report of the user's electrotherapy history. This report may include a number of electrotherapy programs delivered, the time and date of the delivered electrotherapy programs, physiological metrics (such as amount of pain or range of motion) to track the user's response to the electrotherapy, whether the user has met certain electrotherapy or physiological targets (e.g., completing one treatment per day, or deadlifting a target amount of weight), or any other information that reflects the user's health, goals, or use of electrotherapy. The processor 1222 may provide the report to the user via the display 1238, or may send the report electronically to the patient (e.g., via an e-mail account), to a clinician, to a printing device, or to a removable storage medium (such as a USB key). After the processor 1222 provides the report at step 1364, the method can return to step 1320 where the introductory screen is displayed. In another aspect, the method 1300 may end.

If the user does not select the STATISTICS option at step 1362, the method proceeds to step 1366 in which the processor 1222 determines whether the user has selected the INDICATION option. If the user has selected the INDICATION option, the flow diagram 1300 proceeds to step 1368 and the processor 1222 executes an indication/recommendation procedure. In this procedure, the processor may query the user for information about his or her physical health, including any clinical indication or goals to which electrotherapy may be applied. The user may input the requested information to the computing device 1200, and in response, the processor 1222 may provide a recommendation of appropriate electrotherapy programs for the user's indication or goals. This recommendation may be drawn from a database linking indications/goals and electrotherapy programs that is stored locally to the computing device 1200 (e.g., in the data storage 1214) or may be drawn from a remote database (such as the database 1112 of FIG. 11). The database may be populated by clinicians, for example, based on clinical knowledge. The indication/recommendation procedure executed by the processor 1222 at step 1368 may be interactive, and may follow a decision tree in which a sequence of questions are provided to the user based on the user's response to previous questions. In some implementations, the outcome of the indication/recommendation procedure of step 1368 is the identification of a particular electrotherapy program or set of electrotherapy programs targeted to the user's indication or goals. These identified programs may be automatically downloaded to the electrotherapy device 500, or may be presented to the user for his or her selection and review. After the processor 1222 provides the identified programs at the conclusion of step 1368, the processor 1222 can return to step 1320 wherein the introductory screen is displayed. In another aspect, the method 1300 may end.

In some embodiments of method 1300, step 1320 is a starting point, providing the user multiple options, as discussed above. Certain aspects of the method 1300 are cyclic in nature, returning to the introductory screen at step 1320 upon completion of a specific process (e.g., SHOP, STATISITICS, INDICATION functions, or completion or interruption of an electrotherapy program). Accordingly, the introductory screen at step 1320 may be considered both a beginning and an end in various embodiments of the method 1300.

In some implementations of the electrotherapy devices disclosed herein, a conductive gel layer is fixedly attached to the conductive layer in order to improve the conductive interface between the conductive layer and the patient's skin. In other implementations, a gel layer that is separate from the conductive layer is applied to the conductive layer or to the patient's skin prior to bringing the electrotherapy device into electrical contact with the patient's skin. In some implementations, the gel layer is configured to be disposed of after one or more uses and a new gel layer is used with the existing electrotherapy device. For example, a gel layer may be used once for electrotherapy before being discarded. A new gel layer is then applied to the electrotherapy device or to the user's skin prior to starting a new round of electrotherapy treatment. In some such implementations, the gel layer is a hydrogel that crosslinks on a user's skin, instead of being crosslinked in advance in a manufacturing facility. Applying a non-crosslinked gel layer to a patients' skin before applying an electrotherapy device may be suitable in implementations in which the electrotherapy device does not include an integral gel layer between the conductive layer and patients' skin. In such implementations, a non-crosslinked gel layer can be separately applied, crosslinked in place, and then the electrotherapy device can be applied on top of the crosslinked hydrogel.

Figures 14A, 14B, 14C:
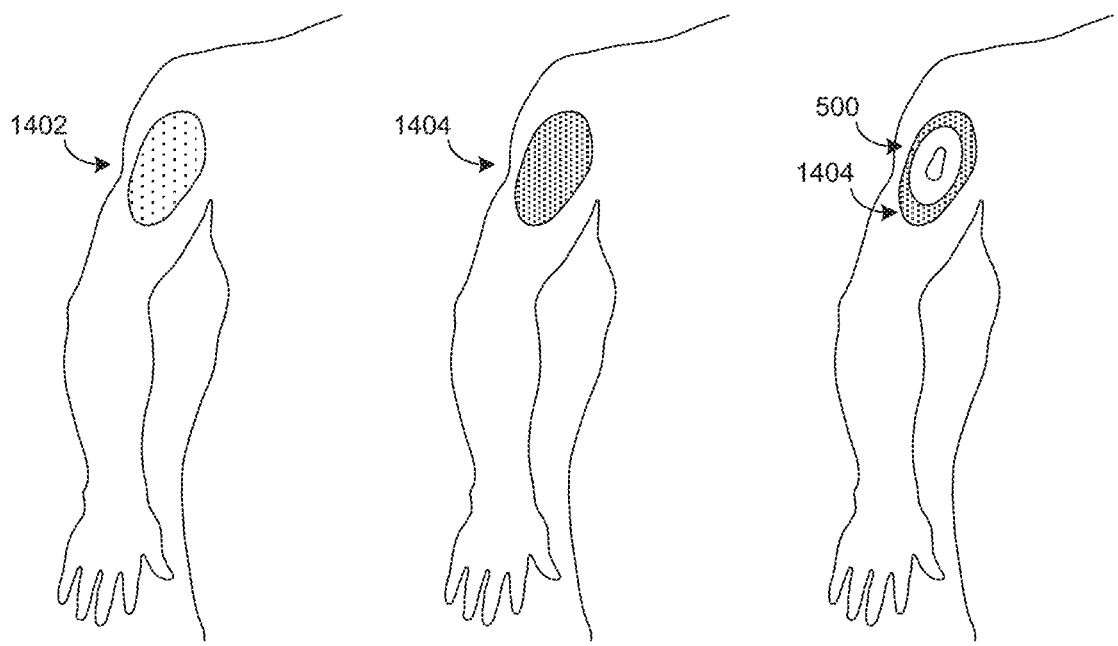
FIGS. 14A-14B are perspective views of a gel layer crosslinking on a user's skin prior to application of an electrotherapy device.
FIG. 14C is a perspective view of an embodiment of an electrotherapy device applied to the crosslinked gel layer of FIGS. 14A-14B.

FIGS. 14A-14C are perspective views of a hydrogel crosslinking on a user's skin prior to application of an electrotherapy device according to embodiments of the present disclosure. In FIG. 14A, a non-crosslinked gel layer 1402 is applied to a desired treatment area on the patients' skin. The non-crosslinked gel layer 1402 applied in FIG. 14A may be delivered to the tissue surface of the patient in any number of ways. In some implementations, the non-crosslinked gel layer 1402 is sprayed onto a user's skin using a pump or aerosol spray structure. In some implementations, the non-crosslinked gel layer 1402 is applied to the user's skin using a container with a roll-on applicator structure. In some implementations, the non-crosslinked gel layer 1402 is applied to the user's skin with a brush or sponge that is integral to, or separate from, a container of the non-crosslinked gel layer.

FIG. 14B depicts the non-crosslinked gel layer 1402 (FIG. 14A) crosslinking in place on the user's skin to form a crosslinked gel layer 1404. In some implementations, the non-crosslinked gel layer 1402 of FIG. 14A crosslinks in the presence of a heat source (e.g., the heat of the patients' body or a separate heat source). In some implementations, the non-crosslinked gel layer 1402 crosslinks when mixed or otherwise in contact with another chemical compound. This additional compound may be sprayed on to the non-crosslinked gel layer 1402 after the non-crosslinked gel layer 1402 has been applied to the patient's skin, or may be mixed with the non-crosslinked gel layer 1402 prior to application to the patients' skin (e.g., similar to the mixing of a tube of epoxy). Once both compounds have been applied to the patient's skin, the patient may then wait for a predetermined period of time for the non-crosslinked gel layer 1402 to cross link into the crosslinked gel layer 1404. In some implementations, the non-crosslinked gel layer 1402 is crosslinked in the presence of an electromagnetic energy source (e.g., an ultraviolet light source or other light source). The electromagnetic energy may come from a dedicated device (e.g., an ultraviolet light wand), or may be integrated into the electrotherapy device, as discussed in additional detail below with reference to FIG. 17.

Once the non-crosslinked gel layer 1402 has been applied to the patient's skin (as shown in FIG. 14A) and has crosslinked into the crosslinked gel layer 1404 (as shown in FIG. 14B), electrotherapy devices described herein, such as the electrotherapy device 500, may be applied to the crosslinked gel layer 1404 (as shown in FIG. 14C). The electrotherapy device 500 is positioned on the patient's skin such that the conductive layer adheres to the crosslinked gel layer 1404. After the desired electrotherapy program has been completed, the user may remove the electrotherapy device 500, leaving the crosslinked gel layer 1404 behind on the skin. The crosslinked gel layer 1404 may then be peeled or washed away from the skin and the electrotherapy device 500 reused with another gel layer at a future time. In some implementations, the strength of the adhesion between the conductive layer of the electrotherapy device 500 and the crosslinked gel layer 1404 makes it easier for the patient to remove the electrotherapy device 500 and the crosslinked gel layer 1404 at the same time, with the crosslinked gel layer 1404 remaining adhered to the conductive layer. In such implementations, the user may separate the crosslinked gel layer 1404 from the conductive layer (e.g., by peeling) and dispose of the crosslinked gel layer 1404, while leaving the electrotherapy device 500 available for use with another crosslinked gel layer 1404 at a future time.

Figures 15A, 15B:
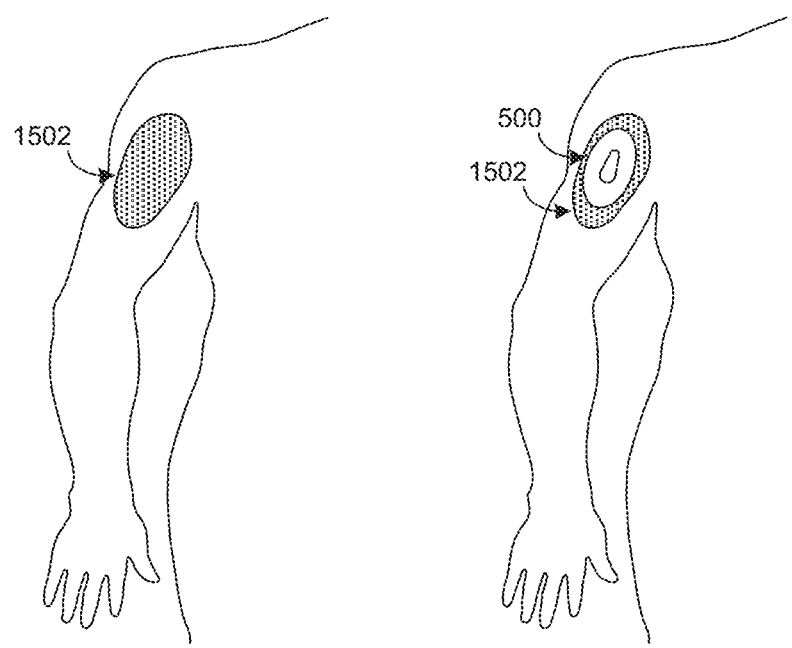
FIGS. 15A-15B are perspective views of a hydrogel patch positioned on a patient's skin prior to and after application of an embodiment of an electrotherapy device.

In some implementations, a gel layer separate from the conductive layer of an electrotherapy device is applied to the patient's skin having previously been crosslinked. In other words, there is no need for the user or the electrotherapy device to apply an additional energy source to the gel layer to achieve crosslinking. FIG. 15A is a perspective view of a previously crosslinked gel layer 1502 positioned on a patient's skin, while FIG. 15B is a perspective view of an electrotherapy device 500 positioned on the crosslinked gel layer 1502.

Figure 16A:
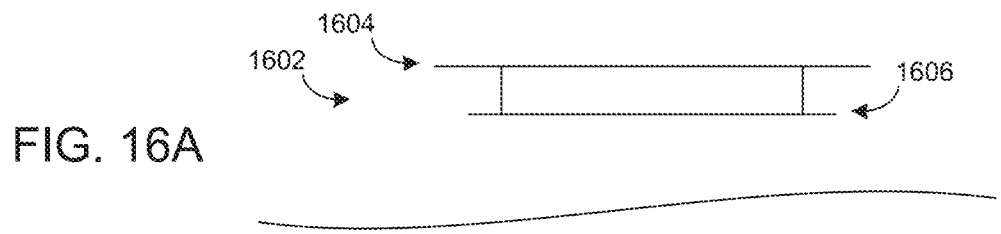
FIGS. 16A-16E are cross-sectional views illustrating application of a hydrogel patch to a user's skin according to an embodiment of the present disclosure.

In some implementations, the crosslinked gel layer 1502 of FIG. 15A is a prepackaged gel layer. The crosslinked gel layer 1502 may be packaged for example, in a foil packet, with a removable backing sheet on one face of the crosslinked gel layer 1502 and a removable cover sheet on the other face of the crosslinked gel layer 1502. FIGS. 16A-16E are cross sectional views of the application of one embodiment of such a prepackaged gel layer 1602 (e.g., hydrogel) to a patient's skin 1608. FIG. 16A depicts the prepackaged gel layer 1602 with a removable backing layer 1604 applied to one face of the prepackaged gel layer 1602 and a removable cover sheet 1606 applied to the other face of the prepackaged gel layer 1602. Removable backing layer 1604 and removable cover sheer 1606 can serve to protect prepackaged gel layer 1602 during storage and shipping.

Figure 16B:
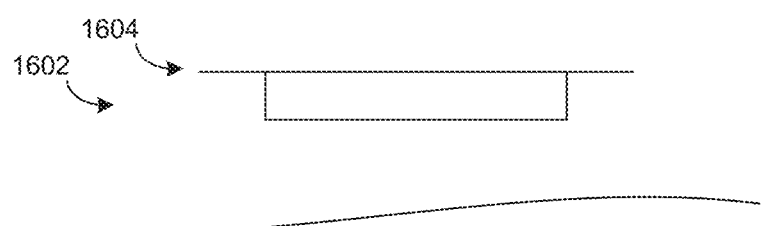
Figure 16C:
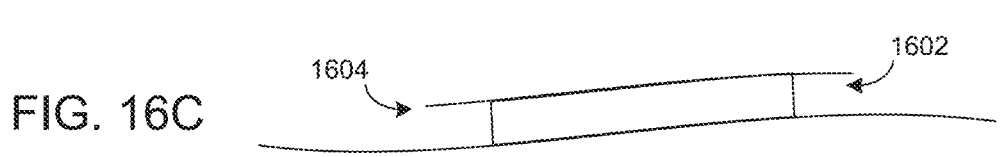
Figure 16D:
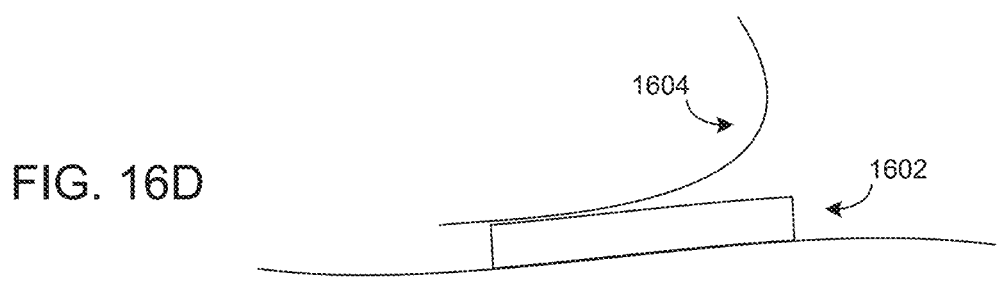
Figure 16E:

In FIG. 16B, the cover sheet 1606 has been removed (e.g., peeled away) from the prepackaged gel layer 1602 and in FIG. 16C, the exposed face of the prepackaged gel layer 1602 has been applied to the patients' skin 1608. In FIG. 16D, the removable backing sheet 1608 is peeled away in direction 1610, leaving the prepackaged gel layer 1602 positioned on the patients' skin 1608, as shown in FIG. 16E.

In some implementations of the gel layers described herein, the perimeter dimensions of the gel layer approximately match the perimeter dimensions of the conductive layer. In implementations in which a prepackaged gel layer is used (such as the prepackaged gel layer 1602 of FIG. 16A-16E), the shape of the prepackaged gel layer and the shape of the conductive layer of the electrotherapy device may be matched. This may allow manufacturers of electrotherapy devices to key their products to particular prepackaged gel layers in order to make is more difficult for unauthorized or inadequate gel layers to be used with the electrotherapy devices.

As indicated above, in some implementations, electrotherapy devices according to embodiments described herein include an energy source for crosslinking a non-crosslinked gel layer. FIG. 17 is a cross-sectional view of an electrotherapy device 1700 with one embodiment of an integrated crosslinking energy source. Similar to other electrotherapy devices described herein, the electrotherapy device 1700 includes a nonconductive top layer 1702, an electronics layer 1712, a nonconductive intermediate layer 1726, a conductive layer 1708 with multiple conductive zones, and two nonconductive elements 1718. The integrated crosslinking energy source shown in this implementation includes two light emitting diodes (LEDs) 1730. The LEDs 1730 emit light of a predetermined wavelength (e.g., an ultraviolet wavelength). In use, a non-crosslinked gel layer that crosslinks in the presence of light of that predetermined wavelength is applied to the patient's skin (e.g. skin 1608), and the electrotherapy device 1700 is applied thereon so that the conductive layer 1708 of the electrotherapy device 1700 adheres to the non-crosslinked gel layer. The LEDs 1730 of the electrotherapy device 1700 can then be activated to begin a crosslinking phase, emitting light of the predetermined wavelength and causing the crosslinking of the non-crosslinked gel layer.

In some implementations, a user presses a single button on the electrotherapy device 1700 to activate the LEDs 1730 for a predetermined period of time, after which the electrotherapy device 1700 turns the LEDs 1730 off. The duration of this predetermined time may be selected to achieve an adequate crosslinking of the non-crosslinked gel layer. In some implementations, an LED or other indicator proximal to the nonconductive top layer 1702 of the electrotherapy device 1700 will illuminate after completion of the crosslinking phase, indicating to the user that an electrotherapy program may begin. In some implementations, the electrotherapy device 1700 transmits a message to the computing device (e.g., the computing device 1200 of FIG. 12) when the crosslinking phase has completed, after which point the user is allowed to initiate an electrotherapy program or an electrotherapy program is automatically initiated.

Figure 18:
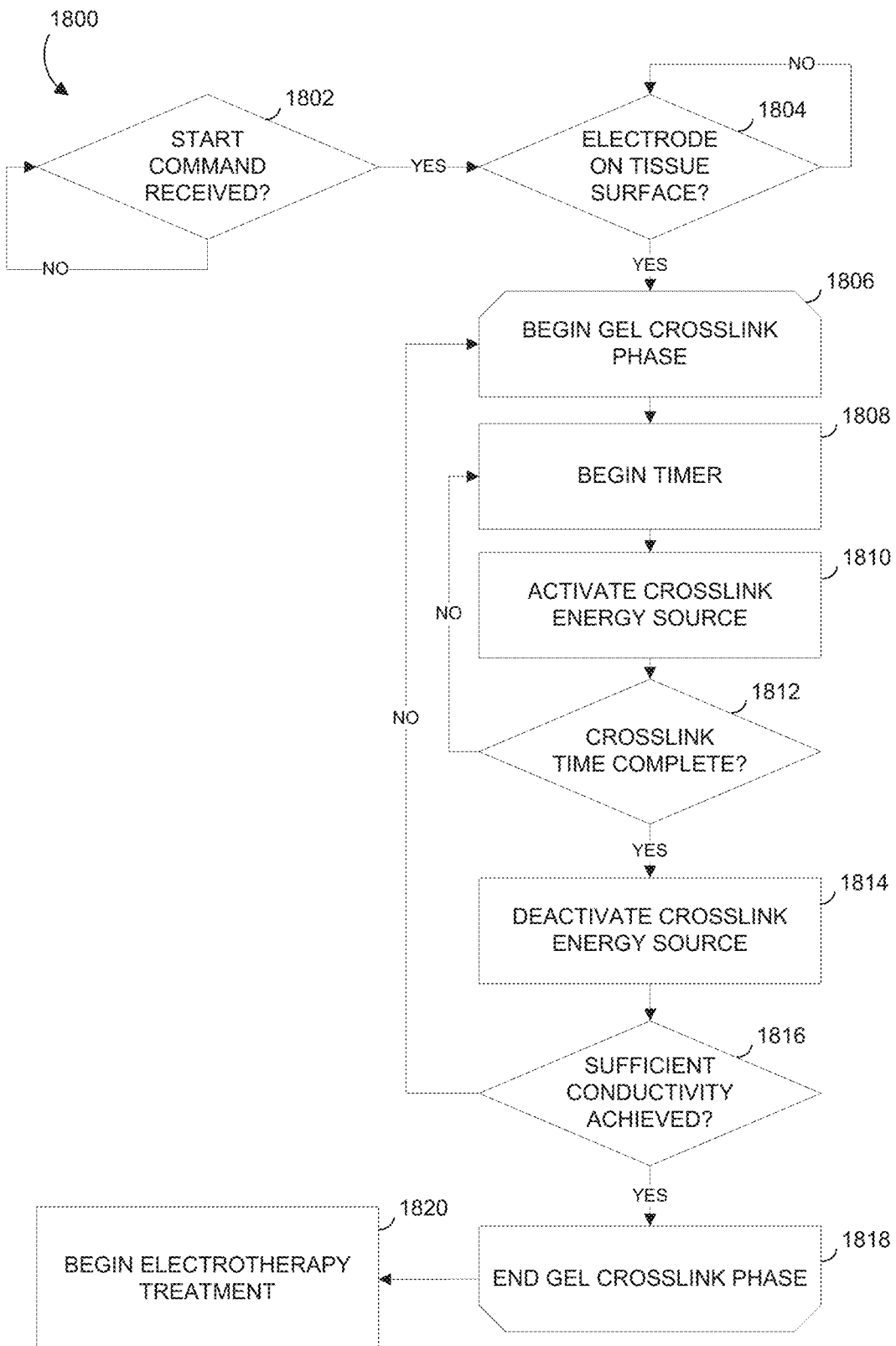
FIG. 18 is a flow diagram illustrating a method of operating an electrotherapy device configured with a crosslinking energy source for in-place crosslinking of a hydrogel according to an embodiment of the present disclosure.

FIG. 18 is a flow diagram illustrating a method 1800 of operating of an electrotherapy device including a crosslinking energy source for in-place crosslinking of a hydrogel (such as the electrotherapy device 1700 of FIG. 17) in accordance with one embodiment of the present disclosure. For ease of illustration, the steps of method 1800 are described as carried out by or within the electrotherapy device 500 of FIG. 5, but any electrotherapy device described herein may implement embodiments of the method 1800.

The method 1800 begins at step 1802, in which the electrotherapy device 500 determines whether a START command has been received. The START command may be a command to initiate a crosslinking phase or a command issued to initiate an electrotherapy program. The START command may be communicated by the user via, for example, the press of a button on the electrotherapy device 500 or a computing device in wireless or wired communication with the electrotherapy device (such as the computing device 1200 of FIG. 12).

The method 1800 next moves to step 1804, in which the electrotherapy device 500 determines whether the conductive layer of the electrotherapy device 500 has been positioned adjacent to the user's skin. This step may be advantageously performed in implementations in which the energy source included in the electrotherapy device 500 should not be activated until the electrotherapy device 500 is in position on the tissue surface (e.g., when the energy source is a source of ultra-violet light).

If the electrotherapy device 500 determines that the conductive layer has been positioned adjacent to the user's skin at step 1804, the method 1800 proceeds to step 1806 in which the electrotherapy device 500 begins a gel crosslink phase. The method 1800 next moves to step 1808, in which the electrotherapy device 500 activates timer circuitry to begin timing. At step 1810, the electrotherapy device 500 activates the crosslinking energy source. As discussed above, the crosslinking energy source may be a source of heat, a source of electromagnetic energy, or any other energy source that can be used to trigger the crosslinking of the non-crosslinked gel layer. If the electrotherapy device 500 determines that the crosslink time has completed at step 1812, the method 1800 proceeds to step 1816 in which the electrotherapy device 500 deactivates the crosslinking energy source.

Moving next to step 1816, the electrotherapy device 500 performs a test to determine whether sufficient conductivity has been achieved between the conductive layer and the patient's tissue. In some implementations, this test includes an impedance test, wherein the electrotherapy device 500 measures the impedance between two conductive zones in the conductive layer. The electrotherapy device 500 may determine that sufficient conductivity has been achieved if the detected impedance is below a threshold. If sufficient conductivity has not been achieved, the electrotherapy device 500 may return to step 1806 and begin the gel crosslink phase again. The electrotherapy device 500 may also illuminate an indicator to communicate to the patient that the initial round of crosslinking has failed, or may send a message to the computing device, or both. If the electrotherapy device 500 determines at step 1816 that sufficient conductivity has been achieved, the gel crosslink phase ends at step 1818 and the electrotherapy program begins at step 1820.

Those of skill will recognize that the various illustrative logical blocks, modules, circuits, and algorithm steps described in connection with the embodiments disclosed herein, including with reference to the electrotherapy devices and systems described herein, for example, may be implemented as electronic hardware, software stored on a computer readable medium and executable by a processor, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure. For example, various illustrative logical blocks, modules, and circuits described in connection with the embodiments disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration. Software associated with such modules may reside in RAM memory, flash memory, ROM memory, EPROM memory, EEPROM memory, registers, a hard disk, a removable disk, a CD-ROM, or any other suitable form of storage medium known in the art. An exemplary storage medium is coupled to the processor such the processor can read information from, and write information to, the storage medium. In the alternative, the storage medium may be integral to the processor. The processor and the storage medium may reside in an ASIC. For example, in one embodiment, a controller, such as but not limited to computing circuitry 126 described with reference to FIG. 1C or a controller 506 described with reference to FIG. 5, comprises a processor (not shown).

It is to be understood that the foregoing description is merely illustrative, and is not to be limited to the details given herein. While several embodiments have been provided in the present disclosure, it should be understood that the disclosed systems, devices, and methods and their components may be embodied in any other specific forms without departing from the scope of the disclosure.

Variations and modifications will occur to those of skill in the art after reviewing this disclosure, where disclosed features may be implemented in any combination and subcombinations (including multiple dependent combinations and subcombinations), with one or more other features described herein. The various features described or illustrated above, including any components thereof, may be combined or integrated in other devices, systems or methods; moreover, certain features may be omitted or not implemented. It will also be appreciated by those of skill in the art that parts described with reference to one embodiment are interchangeable with other embodiments; one or more parts from a depicted embodiment can be included with other depicted embodiments in any combination. For example, any of the various components described herein and/or depicted in the Figures may be combined, interchanged, or excluded from other embodiments. Thus, while the present disclosure has described certain practical embodiments, it is to be understood that the invention is not limited to the disclosed embodiments, but, on the contrary, is intended to cover various modifications and equivalent arrangements included within the scope of the appended claims, and equivalents thereof.

What is claimed is:

1. A method of performing non-invasive electrical stimulation, the method comprising:
providing a non-invasive electrical stimulation device, the device comprising:
at least one remote electrode that can be bent to fit to a user's body, the remote electrode having a conductive gel attached to a conductive layer of the remote electrode, the at least one remote electrode electrically connected to pulse generation circuitry;
the pulse generation circuitry in electrical communication with communication circuitry, the communication circuitry configured to receive and process pulse generation control signals from a computing device;
detecting the presence of the non-invasive electrical stimulation device by the computing device;
presenting, on a display of the computing device, a plurality of pulse generation control signal options available for transmission to the non-invasive electrical stimulation device;
wirelessly transmitting a selection of the pulse generation control signals from the computing device to the communication circuitry;
presenting on the display of the computing device, a visual instruction on where to place the at least one remote electrode on the user's body based on the selection of the pulse generation control signals;
positioning the at least one remote electrode on to the user's body such that the conductive gel is against the user's body; and
delivering electrical stimulation waveforms through the at least one remote electrode according to instructions encoded in the pulse generation control signals.

2. The method of claim 1, further comprising receiving a user command input and modifying at least one of the electrical stimulation waveforms as a result of the user command input.

3. The method of claim 1, further comprising providing the electrical stimulation waveforms in real time as the pulse generation control signals are received at the pulse generation circuitry.

4. The method of claim 1, wherein transmitting the pulse generation control signals from the computing device comprises transmitting the pulse generation signals from one of a cellular telephone device, a portable media player, a personal digital assistant, a tablet computer, or an internet access device.

5. The method of claim 1, further comprising encoding by a processor, into a signal for transmission to the computing device, at least one of a time duration of delivered non-invasive electrical stimulation, a pulse count of delivered non-invasive electrical stimulation, and a number of delivered non-invasive electrical stimulation sessions.

6. The method of claim 1, further comprising tracking, by timer circuitry in the non-invasive electrical stimulation device, the amount of non-invasive electrical stimulation delivered.

7. The method of claim 6, further comprising storing, in a memory device of the non-invasive electrical stimulation device, at least one of a time duration of delivered non-invasive electrical stimulation, a pulse count of delivered non-invasive electrical stimulation, or a number of delivered non-invasive electrical stimulation sessions.

8. The method of claim 1, further comprising receiving at the non-invasive electrical stimulation device the pulse generation control signals, from the computing device, in response to a user command input on an interface of the computing device.

9. The method of claim 8, wherein the user command input includes a non-invasive electrical stimulation start command.

10. The method of claim 1, further comprising receiving, at the non-invasive electrical stimulation device, a second set of pulse generation control signals, transmitted from the computing device, through a wired connection and wired communication circuitry of the non-invasive electrical stimulationel device.

11. The method of claim 10, further comprising deactivating one of the wireless communication circuitry and the wired communication circuitry when the other of the wireless communication circuitry and the wired communication circuitry is active.

12. The method of claim 1, further comprising receiving, at the computing device, at least one user input control for controlling the electrical stimulation waveforms, the user input control is one of more of intensity of the electrical stimulation waveforms, a duration of the electrical stimulation waveforms, or power of the electrical stimulation waveforms.

13. The method of claim 12, wherein the plurality of pulse generation control signal include a plurality of programmed electrotherapy programs.

14. The method of claim 1, further comprising receiving at the computing device a user input command including a purchase request for a new electrotherapy program.

15. The method of claim 1, further comprising receiving at the computing device a user input command including a purchase request for consultation on therapy regimens.

16. The method of claim 1, further comprising a power source attached to the at least one remote electrode.

17. The method of claim 16, wherein the power source is a rechargeable Lithium Polymer battery.

18. The method of claim 16, wherein the computing device displays an indication when the power source does not have enough power to complete the selection of the pulse generation control signals.

* * * * *